(12) United States Patent
Headley et al.

(10) Patent No.: US 11,001,490 B2
(45) Date of Patent: May 11, 2021

(54) EXTRACTION SYSTEM FROM A CLOSED LOOP SYSTEM

(71) Applicant: BERICAP Holding GmbH, Budenheim (DE)

(72) Inventors: Thomas R. Headley, Roanoke, IN (US); Matthew H. Gevers, Fort Wayne, IN (US); Brock E. Holley, Fort Wayne, IN (US)

(73) Assignee: BERICAP Holding GmbH, Budenheim (DE)

( * ) Notice: Subject to any disclaimer, the term of this patent is extended or adjusted under 35 U.S.C. 154(b) by 0 days.

(21) Appl. No.: 16/364,719

(22) Filed: Mar. 26, 2019

(65) Prior Publication Data

US 2019/0308867 A1 Oct. 10, 2019

Related U.S. Application Data

(60) Provisional application No. 62/655,402, filed on Apr. 10, 2018.

(51) Int. Cl.
*B67D 3/00* (2006.01)
*B67D 7/74* (2010.01)
(Continued)

(52) U.S. Cl.
CPC ....... *B67D 3/0045* (2013.01); *A61M 5/31505* (2013.01); *B67D 3/0025* (2013.01);
(Continued)

(58) Field of Classification Search
CPC .. B67D 3/0045; B67D 3/0025; B67D 7/0227; B67D 7/0294; B67D 7/344; B67D 7/74;
(Continued)

(56) References Cited

U.S. PATENT DOCUMENTS 103,027 A * 5/1870 Dieulafoy ......... A61M 5/31505
                                                    604/220
1,647,538 A * 11/1927 Murphy ................... F16N 3/12
                                                    141/352
(Continued)

FOREIGN PATENT DOCUMENTS

DE    20 2006 014 061 U1    12/2006
DE    102007002983 A1 *      7/2008    ........... B65D 47/248
(Continued)

OTHER PUBLICATIONS

International Search Report and Written Opinion; Application No. PCT/US2018/025016; dated Jun. 19, 2018.
(Continued)

*Primary Examiner* — Timothy L Maust
*Assistant Examiner* — James R Hakomaki
(74) *Attorney, Agent, or Firm* — Barnes & Thornburg LLP

(57) ABSTRACT

The present disclosure provides a metered dosing assembly configured to dispense a volume of fluid into a container that is selectively sealed by a closure valve having a closure valve member that is movable between sealed and unsealed positions with respect to the container. The metered dosing assembly includes a housing having an interior cavity. A valve is locatable at an end of the housing. The valve includes a valve member, a pin extending from the valve member, and at least one spring leg attachable to the valve member. The pin extends from the valve member and is configured to engage the closure valve member of the closure valve to move the closure valve member to the unsealed position and move the valve member to an open position with respect to the housing. When the valve member is moved to the open position and the closure valve member is moved to the unsealed position, fluid communi-
(Continued)

cation is made between the metered dosing assembly and the container.

12 Claims, 19 Drawing Sheets

(51) Int. Cl.
   *G01F 19/00* (2006.01)
   *B67D 7/02* (2010.01)
   *A61M 5/315* (2006.01)
   *B67D 7/34* (2010.01)

(52) U.S. Cl.
   CPC ......... *B67D 7/0227* (2013.01); *B67D 7/0294* (2013.01); *B67D 7/344* (2013.01); *B67D 7/74* (2013.01); *G01F 19/00* (2013.01)

(58) Field of Classification Search
   CPC .... A61M 5/31505; G01F 10/00; G01F 19/00; G01F 19/005; G01F 11/025; G01F 11/023; B67C 3/28
   USPC .......................................................... 141/27
   See application file for complete search history.

(56) References Cited

U.S. PATENT DOCUMENTS

| | | | |
|---|---|---|---|
| 2,869,543 A * | 1/1959 | Ratcliff | A61M 5/19 604/90 |
| 3,353,718 A * | 11/1967 | McLay | A61M 5/31586 222/158 |
| 4,081,006 A | 3/1978 | Crowell et al. | |
| 4,313,477 A | 2/1982 | Sebalos | |
| 4,508,173 A | 4/1985 | Read | |
| 4,750,373 A * | 6/1988 | Shapiro | B01L 3/0234 73/864.87 |
| 4,948,014 A * | 8/1990 | Rutter | B65D 77/067 137/614.04 |
| 5,029,624 A | 7/1991 | McCunn et al. | |
| 5,046,645 A * | 9/1991 | Hagan | B65D 83/48 222/394 |
| 5,215,538 A * | 6/1993 | Larkin | A61M 39/26 137/516.13 |
| 5,300,041 A * | 4/1994 | Haber | A61M 5/24 604/207 |
| 5,360,413 A * | 11/1994 | Leason | A61M 39/26 137/843 |
| 5,509,433 A * | 4/1996 | Paradis | A61J 1/18 137/1 |
| 5,573,516 A * | 11/1996 | Tyner | A61M 39/26 137/843 |
| 5,641,012 A | 6/1997 | Silversides | |
| 5,884,648 A * | 3/1999 | Savage | B67D 7/0294 137/1 |
| 5,947,171 A | 9/1999 | Woodruff | |
| 5,960,840 A | 10/1999 | Simmel et al. | |
| 5,996,653 A | 12/1999 | Piccinino, Jr. | |
| 6,170,543 B1 | 1/2001 | Simmel et al. | |
| 6,213,448 B1 * | 4/2001 | Hayakawa | F16K 1/36 251/129.15 |
| 6,220,482 B1 | 4/2001 | Simmel et al. | |
| 6,418,987 B1 | 7/2002 | Colasacco | |
| 6,770,056 B2 * | 8/2004 | Price | G01F 11/023 222/43 |
| 7,121,437 B2 | 10/2006 | Kasting | |
| 7,392,922 B2 | 7/2008 | Vanstaan et al. | |
| 7,546,857 B2 | 6/2009 | Chadbourne et al. | |
| 7,686,194 B2 | 3/2010 | Kasting | |
| 8,925,593 B2 | 1/2015 | Lamboux | |
| 9,850,058 B2 * | 12/2017 | Kolonia | A61M 5/2448 |
| 9,976,660 B2 * | 5/2018 | Stanton | A61M 39/26 |
| 10,189,614 B2 | 1/2019 | Pruiett | |
| 10,365,141 B2 | 7/2019 | Freiburger et al. | |
| 2002/0139867 A1 | 10/2002 | Bulloch et al. | |
| 2006/0173439 A1 * | 8/2006 | Thorne, Jr. | A61M 5/14244 604/506 |
| 2007/0072146 A1 | 3/2007 | Pierson | |
| 2013/0160891 A1 * | 6/2013 | Vassallo | B65D 47/0804 141/27 |
| 2015/0276069 A1 | 10/2015 | Saragosa et al. | |
| 2015/0321836 A1 | 11/2015 | Speas | |
| 2015/0359969 A1 * | 12/2015 | Armstrong | A61M 5/31526 604/221 |
| 2016/0030288 A1 | 2/2016 | Vassallo et al. | |
| 2016/0067143 A1 * | 3/2016 | Ferrara | A61J 1/1425 604/404 |
| 2018/0093040 A1 * | 4/2018 | Thorne, Jr. | A61M 5/19 |
| 2018/0207061 A1 * | 7/2018 | Fox | B65D 50/046 |
| 2018/0333690 A1 * | 11/2018 | Freiburger | G01F 11/38 |

FOREIGN PATENT DOCUMENTS

| | | |
|---|---|---|
| DE | 10 2009 019 933 A1 | 11/2010 |
| DE | 10 2015 103 754 B3 | 2/2016 |
| DE | 20 2016 105 715 U1 | 1/2017 |
| DE | 20 2013 103 516 U1 | 12/2018 |
| WO | WO 2011/058541 A1 | 5/2011 |
| WO | WO2017/201366 A1 | 11/2017 |

OTHER PUBLICATIONS

International Search Report and Written Opinion; Application No. PCT/US2018/015847; dated May 9, 2018.
International Search Report and Written Opinion of the International Searching Authority; Application No. PCT/US2017/033475; dated Aug. 14, 2017.
International Preliminary Report on Patentability and Written Opinion, Application No. PCT/US2017/033475; dated Nov. 20, 2018.
Extended EP Search Report: 19167140.3-1018/3552641—Tuthill Corporation—dated Nov. 27, 2019.
Partial EP Search Report: 19167140.3-1018—Tuthill Corporation—dated Aug. 16, 2019.
Modified Abstract 19167140.3—Undated.

* cited by examiner

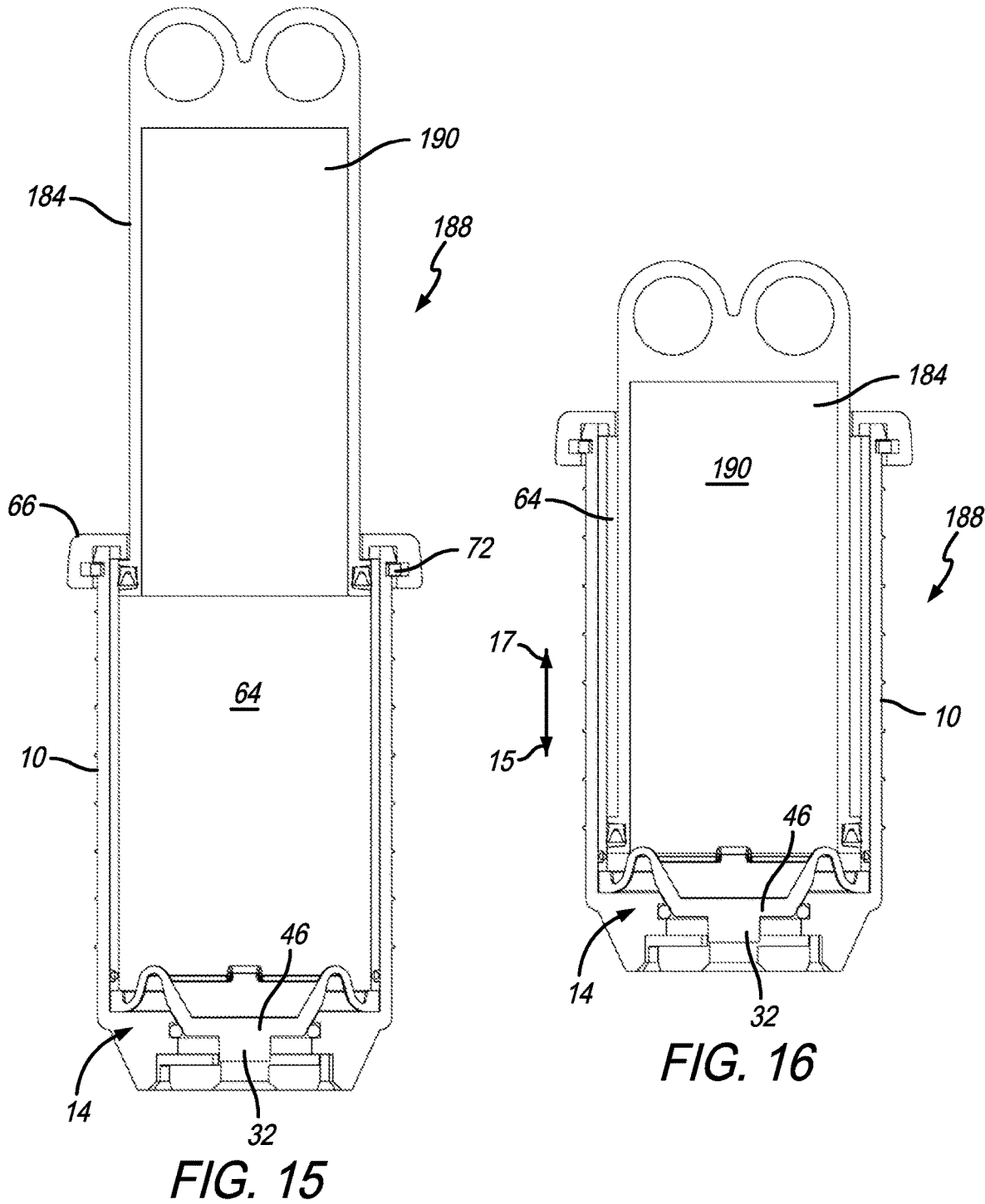

EXTRACTION SYSTEM FROM A CLOSED LOOP SYSTEM

RELATED APPLICATIONS

The present Application is related to and claims priority to U.S. Provisional Patent Application, Ser. No. 62/655,402, filed on Apr. 10, 2018, entitled "Extraction System From A Closed Loop System." The subject matter disclosed in that Provisional Application is hereby expressly incorporated into the present Application.

TECHNICAL FIELD AND SUMMARY

The present disclosure relates to closed-loop fluid transfer mechanisms, and particularly to accessories that dispense specific amounts of fluid into a closed-loop supply container.

Due to the dangers of certain chemical fluids, it is sometimes necessary to limit the fluids' ability to come into contact with any person or thing prior to its intended use. In some instances, however, such fluids need to be transferred from one container to another. For example, instances may arise where a hazardous fluid may need to be transferred from a bottle into a tank. This is why closed loop fluid transfer systems have been developed over the years. Such a system includes a dispensing container that connects to a receiving container to effectuate transfer between same without any fluid exiting the connection between the containers. This system prevents opening the dispensing container until it connects with the receiving container.

Examples of connectors that have been developed to control dispensing chemical and/or hazardous fluid include U.S. Pat. No. 5,960,840 ('840 patent), entitled "Controlled Product Dispensing System," issued Oct. 5, 1999, and U.S. Pat No. 6,170,543 ('543 patent), entitled "Controlled Product Dispensing System," issued Jan. 9, 2001, the disclosures of which are herein incorporated by reference in their entirety. They disclose closure and valve tank adaptors that facilitate direct fluid transfer from one container to another. Also known, is a volumetric inductor/eductor including U.S. patent application Ser. No. 10/103,109, entitled "Volumetric Inductor/Eductor," filed Mar. 21, 2002, and published as U.S. Patent Publication No. U.S. 2002/0139867 ('867 publication), the disclosure which is also herein incorporated by reference in its entirety.

An illustrative embodiment of the present disclosure provides a metered dosing assembly configured to dispense a volume of fluid into a container that is selectively sealed by a closure valve having a closure valve member that is movable between sealed and unsealed positions with respect to the container. The metered dosing assembly comprises: a housing having an interior cavity and first and second ends; a plunger base selectively locatable adjacent the first end of the housing; wherein the plunger base is movable within the interior cavity of the housing to change the size of the interior cavity that holds the volume of fluid; and a valve locatable at the second end of the housing; wherein the valve includes a valve member, a pin extending from the valve member, and at least one spring leg attachable to the valve member; wherein the pin extending from the valve member is configured to engage the closure valve member to move the closure valve member to the unsealed position; wherein the valve member is movable to an open position with respect to the housing when the pin extending from the valve member is engaged with the closure valve member of the closure valve; and wherein, when the valve member is moved to the open position and the closure valve member is moved to the unsealed position, fluid communication is made between the metered dosing assembly and the container.

In the above and other illustrative embodiments, the metered dosing assembly may further comprise: a plunger arm that extends from the plunger base and exterior of the first end of the housing to move the plunger base within the interior cavity to change the size of the interior cavity that holds the volume of fluid; a seal member located between the plunger base and an interior wall of the interior cavity of the housing; a stop located adjacent the first end of the housing to limit movement of the plunger base inside the interior cavity of the housing; the at least one spring leg is a plurality of spring legs; a base located at the second end of the housing, wherein the base includes an opening to the exterior of the housing, and wherein the valve member of the valve is movable with respect to the opening between the open position and a closed position; the valve member of the valve is moved towards the interior cavity of the housing when moved to the open position; the valve further includes a valve base that encircles at least a portion of the valve member, the at least one spring leg, and a space locatable adjacent the valve member and the at least one spring leg; the housing includes a key structure and the valve includes a key structure corresponding to the key structure of the housing, wherein the key structure of the housing abuts the key structure of the valve to limit the positing of the valve within the interior cavity of the housing; the plunger arm includes a second interior cavity that is in fluid communication with the interior cavity of the housing to increase a total volume size of the metered dosing assembly available to hold the volume of fluid; the plunger arm includes a plurality of teeth configured to engage at least one thread on a collar such that as the at least one thread on the collar moves, the plunger arm and plunger base move to change the size of the interior cavity that holds the volume of fluid; a key member located adjacent the first end of the housing, wherein the key member includes an opening that receives at least a portion of plunger arm and at least one tab that engages at least one portion of the housing, wherein, as the at least one thread on the collar moves, the collar rotates to move the plunger base linearly within the interior cavity of the housing, and wherein the key member located adjacent the first end of the housing prevents the plunger arm and plunger base from rotating with the collar; and the plunger arm includes a plurality of flanges and each of the plurality of flanges includes a plurality of teeth, each of the plurality of teeth on the plurality of flanges is configured to engage at least one thread on a collar such that, as the at least one thread on the collar moves, the plunger arm and plunger base move to change the size of the interior cavity that holds the volume of fluid.

Another illustrative embodiment of the present disclosure provides a metered dosing assembly configured to dispense a volume of fluid into a container that is selectively sealed by a closure valve having a closure valve member that is movable between sealed and unsealed positions with respect to the container. The metered dosing assembly comprises: a housing having an interior cavity; and a valve locatable at an end of the housing; wherein the valve includes a valve member, a pin extending from the valve member, and at least one spring leg attachable to the valve member; wherein the pin extending from the valve member is configured to engage the closure valve member of the closure valve to move the closure valve member to the unsealed position and move the valve member to an open position with respect to the housing; and wherein when the valve member is moved to the open position, and the closure valve member is moved to the unsealed position, fluid communication is made between the metered dosing assembly and the container.

In the above and other illustrative embodiments, the metered dosing assembly may further comprise: a base located at the end of the housing, wherein the base includes an opening to the exterior of the housing, and wherein the valve member of the valve is movable with respect to the opening between the open position and a closed position; the valve member of the valve is moved towards the interior cavity of the housing when moved to the open position; the valve further includes a valve base that encircles the valve member, the at least one spring leg, and a space locatable adjacent the valve member and the at least one spring leg; and the housing includes a key structure and the valve includes a key structure corresponding to the key structure of the housing, wherein the key structure of the housing abuts the key structure of the valve to limit the location positing of the valve within the interior cavity of the housing.

Another illustrative embodiment of the present disclosure provides a metered dosing assembly configured to dispense a volume of fluid into a container that is selectively sealed by a closure valve having a closure valve member that is movable between sealed and unsealed positions with respect to the container. The metered dosing assembly comprises: a housing having an interior cavity and first and second ends; a plunger base selectively locatable adjacent the first end of the housing; wherein the plunger base is movable within the interior cavity of the housing to change the size of the interior cavity that holds the volume of fluid; and a valve locatable at the second end of the housing; wherein the valve includes a valve member; and wherein, when the valve member is moved to an open position and the closure valve member is moved to the unsealed position, fluid communication is made between the metered dosing assembly and the container.

In the above and other illustrative embodiments, the metered dosing assembly may further comprise a plunger arm that extends from the plunger base and exterior of the first end of the housing to move the plunger base within the interior cavity to change the size of the interior cavity that holds the volume of fluid.

Additional features and advantages of the extraction system will become apparent to those skilled in the art upon consideration of the following detailed descriptions of carrying out the extraction system as presently perceived.

BRIEF DESCRIPTION OF DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels may be repeated among the figures to indicate corresponding or analogous elements.

FIG. 15 is an elevational cross-sectional view of the telescoping dosing syringe;

FIG. 16 is another elevational cross-sectional view of the telescoping dosing syringe;

Corresponding reference characters indicate corresponding parts throughout the several views. The exemplification set out herein illustrates embodiments of the extraction system, and such exemplification is not to be construed as limiting the scope of the extraction system in any manner.

DETAILED DESCRIPTION OF THE DRAWINGS

Figure 1:
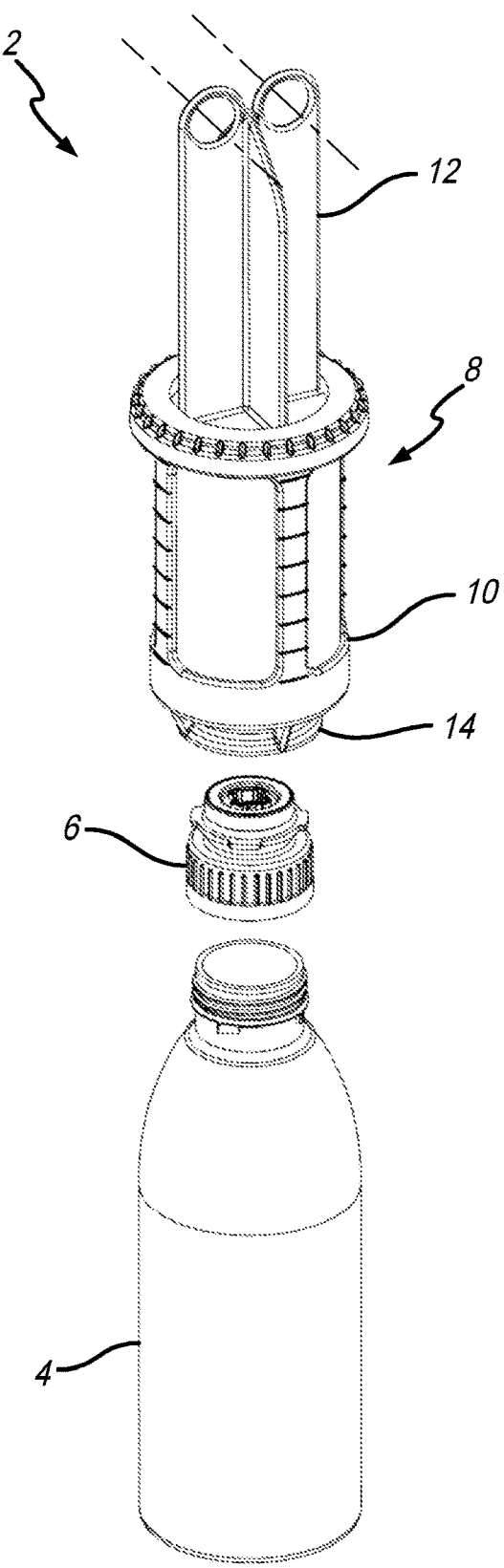
FIG. 1 is an exploded view of a metering system for a closed-loop system, according to an embodiment of the present disclosure.

The figures and descriptions provided herein may have been simplified to illustrate aspects that are relevant for a clear understanding of the herein described devices, systems, and methods, while eliminating for the purpose of clarity, other aspects that may be found in typical devices, systems, and methods. Those of ordinary skill may recognize that other elements and/or operations may be desirable and/or necessary to implement the devices, systems, and methods described herein. Because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Again, examples of connectors that have been developed to control dispensing chemical and/or hazardous fluid include U.S. Pat. No. 5,960,840 ('840 patent), entitled "Controlled Product Dispensing System," issued Oct. 5, 1999, and U.S. Pat. No. 6,170,543 ('543 patent), entitled "Controlled Product Dispensing System," issued Jan. 9, 2001, the disclosures of which are herein incorporated by reference in their entirety. They disclose closure and valve tank adaptors that facilitate direct fluid transfer from one container to another. Also known, is a volumetric inductor/eductor including U.S. patent application Ser. No. 10/103,109, entitled "Volumetric Inductor/Eductor," filed Mar. 21, 2002, and published as U.S. Patent Publication No. U.S. 2002/0139867 ('867 publication), the disclosure which is also herein incorporated by reference in its entirety.

Under some circumstances, a measured amount of fluid is needed to be transferred from one container to another in a closed system. Accordingly, an illustrative embodiment of the present disclosure is directed to a metering extraction and dispensing device for a closed loop system. In an illustrative embodiment, the metering extraction and dispensing device is a dosing dispenser or syringe configured to engage a valve to receive a measured amount of fluid. The dispenser or syringe may also engage another valve on a container to actuate and dispense the fluid into the container. The dispenser or syringe may have graduations on it and employ a mechanical means to define or limit the amount of fluid that enters it. Illustratively, the dispenser or syringe may include a plunger movable within a cylinder. This movement either reduces or expands the volume of fluid that may be received in the cylinder. In other words, the position of the plunger sets the volume of fluid that may be held in the cylinder. Gravity typically causes the fluid to drain from the cylinder and into the container. In a further embodiment, however, the plunger may be used to dispense the fluid from the cylinder and into the container. In yet another embodiment, the plunger may include a cavity to receive additional fluid beyond the amount held in the syringe itself.

An exploded view of an illustrative metering system 2 used for a closed-loop system is shown in FIG. 1. Metering system 2 includes container 4, closure valve 6, and adjustable dosing dispenser or syringe assembly 8. Illustrative dosing syringe 8 is configured to couple to closure valve 6 which is attached to container 4. Such coupling between dosing syringe 8 and closure valve 6 causes dosing syringe 8 to selectively open closure valve 6 to allow a metered amount of fluid that is located in dosing syringe 8 to be deposited through closure valve 6 and into container 4. This means that despite being a closed system (i.e., fluid is not exposed to the outside environment), a specifically measured amount of fluid can be deposited into container 4. This may be useful in applications where a measured amount of fluid chemical concentrate needs to be extracted and deposited into a container to dilute a second fluid such as water.

Illustratively, dosing syringe 8 may include a syringe housing 10 and a plunger 12. Syringe housing 10 may be graduated per units of volume. Plunger 12 adjusts the amount of volume available in syringe housing 10 by adjusting the available space by displacing the air from syringe housing 10. Drawing back plunger 12, with the end of dosing syringe 8 submersed in fluid, may only allow that fluid to enter the available space created in syringe housing 10 rather than air. With closure valve 6 attached to container 4, check valve mechanism 14 on dosing syringe 8 may be opened when coupled to closure valve 6 to create a fluid passageway between syringe housing 10 and the interior of container 4.

Figure 2:
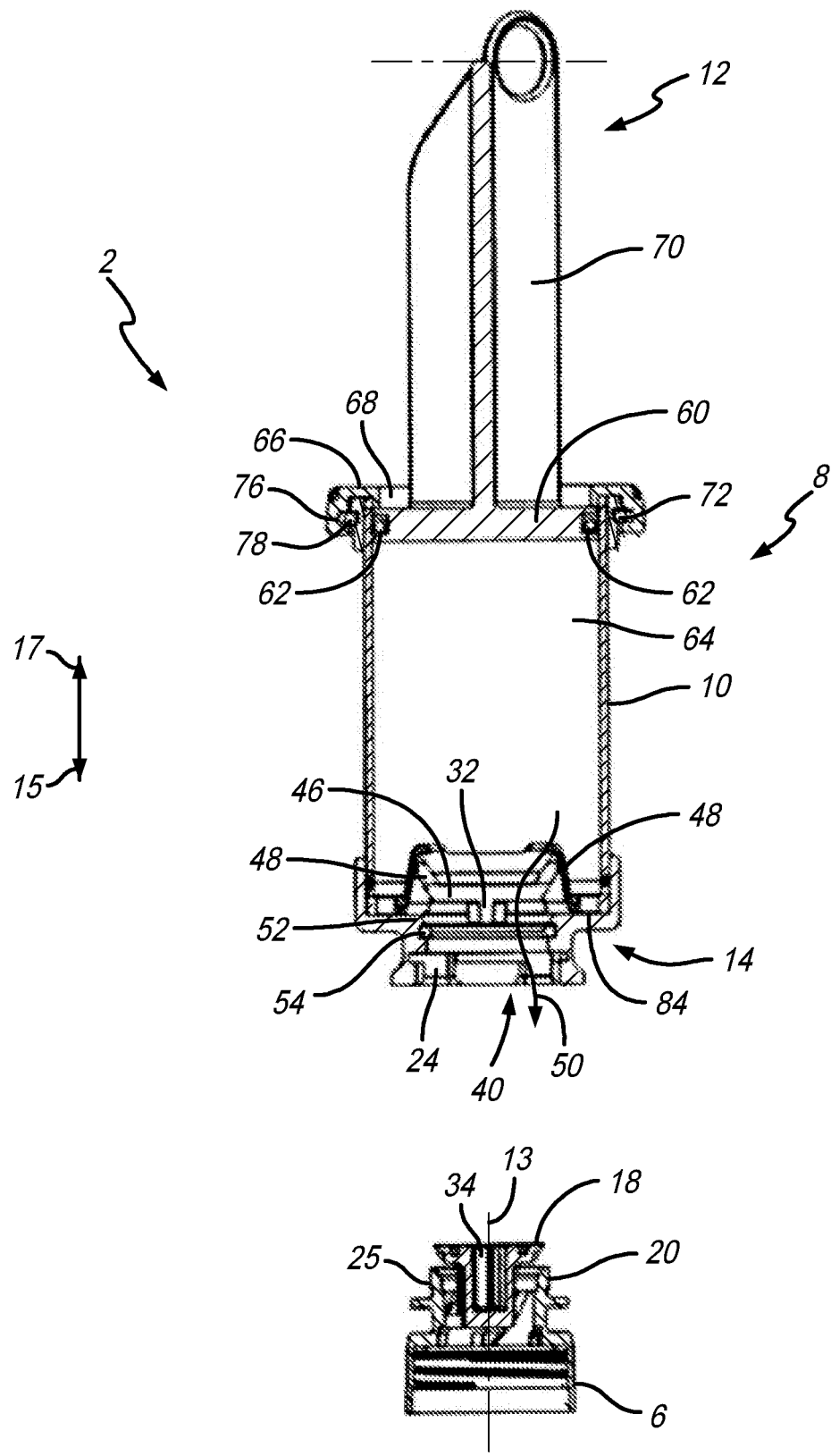
FIG. 2 is an exploded elevational, cross-sectional view of an adjustable dosing dispenser or syringe and a closure valve.

An exploded elevational cross-sectional view of adjustable dosing syringe 8 and closure valve 6 is shown in FIG. 2. With respect to closure valve 6, it includes the same or similar structures as closure valve 2 disclosed in U.S. patent application Ser. No. 15/598,896, entitled "Measuring Adapter Assembly For Closed Loop Fluid Transfer System," filed on May 18, 2017, the entire disclosure of which is herein incorporated by reference. Accordingly, valve member 18 is configured to move in directions 15 and 17 relative to housing 20. Similar to U.S. patent application Ser. No. 15/598,896, closure valve 6 is illustratively attached to container 4 via mating threads. Closure valve 6 acts as a cap to container 4 preventing its contents from exiting unless closure valve 6 is open. In that regard, valve member 18 selectively covers closure valve 6. Helical slots in closure valve 6 are configured to receive fingers that are part of valve member 18. When valve member 18 is caused to rotate, the fingers located in the corresponding helical slots will move linearly thereby opening closure valve 6.

A receptacle 34 of closure valve 6 is disposed in valve member 18. Receptacle 34 is configured to engage key pin 32 of check valve mechanism 14 from dosing syringe 8. Container 4 and closure valve 6 rotate with respect to both valve member 18 and dosing syringe 8. This causes valve member 18 to move in direction 17 and open closure valve 6. This allows fluid communication between dosing syringe 8 and container 4. A skilled artisan upon reading this disclosure shall appreciate that it is possible for the remainder of closure valve 6 (along with container 4) to rotate with respect to valve member 18. This will have the same effect of opening valve member 18.

With respect to check valve mechanism 14, it includes slots 24 and opening 40 configured to receive a portion of closure valve 6. A plurality of illustrative spring legs 48 operate as living hinges to allow valve member 46 to also move between open and closed positions along with valve member 18. In illustrative embodiments, the hinges may be made of polypropylene or other like material. It is further appreciated that surrounding valve member 46 is a web to maintain a seal between dosing syringe 8 and closure valve 6 unless passage opening 50 is formed between the periphery of valve member 46 and wall 52. Illustratively, a seal 54 may be positioned between valve member 46 and wall 52 to maintain a seal between dosing syringe 8 and the outside environment. The hinges have memory when flexed so they will bias to their closed position unless pushed open by valve member 18. In an alternate embodiment, a spring may be employed. But a spring will occupy volume in the syringe which may not be wanted in certain applications. It is still further appreciated that seal 54 may be an O-ring, u-cup, or other like seal.

Plunger 12 illustratively includes a plunger base 60 and seal 62 located about its periphery to provide a movable barrier within interior cavity 64. By moving plunger 12 in either direction 15 or 17, the internal volume of interior cavity 64 may be reduced or increased. Plunger 12 may be moved in direction 17 only to the extent needed to fill interior cavity of dosing syringe 8 with a specific volume of fluid. Then, when it is time to dispense the fluid into another container in a closed-loop system, moving plunger 12 in direction 15 effectively pushes the fluid out of interior cavity 64. That said, fluid cannot be expelled from opening 40 through any passage opening 50 if valve member 46 is not raised in direction 17 to an open position. When this is not the case, any pressure created by plunger 12 against the fluid in direction 15 will create a force against valve member 46 to a closed position. This keeps the fluid sealed inside interior cavity 64 until valve member 46 is moved to an open position.

Also shown in this view is plunger stop 66 located opposite check valve mechanism 14. An opening 68 in plunger stop 66 allows plunger arm 70 to extend therethrough to be manipulated by an operator. A retaining ring 72 is fitted into slots 76 and 78 formed in plunger stop 66 and syringe housing 10, respectively. In this configuration, plunger stop 66 prevents plunger 12 from extending in direction 17 so far as to extricate itself from interior cavity 64. It also provides a defined maximum volume for interior cavity 64.

Figure 3:
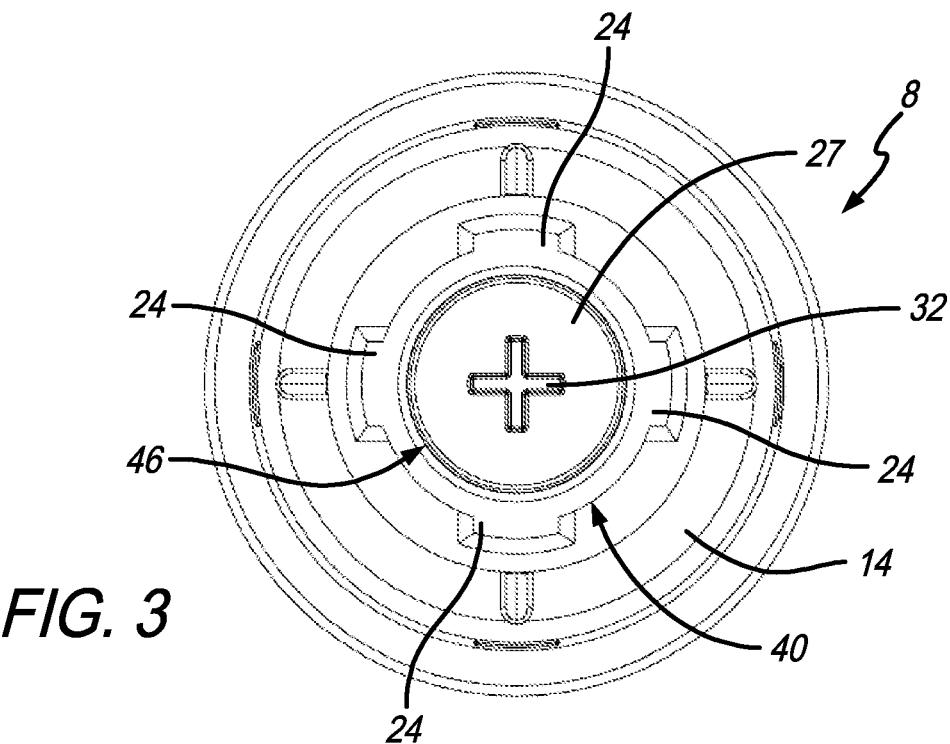
FIG. 3 is an underside view of the adjustable dosing syringe.
Figure 4:
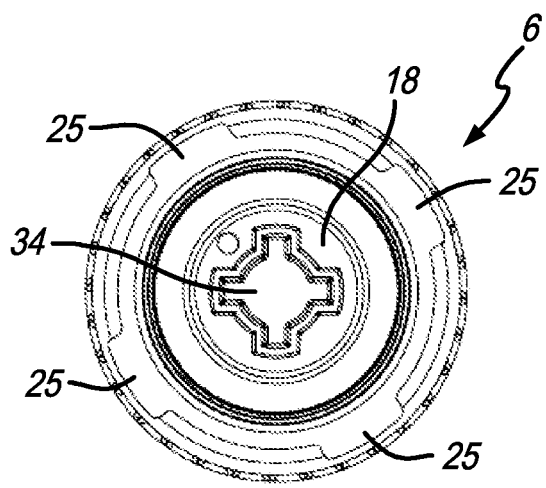
FIG. 4 is a top view of a closure valve.

An underside view of adjustable dosing syringe 8 is shown in FIG. 3 and a top view of closure valve 6 is shown in FIG. 4. These structures are similar to that shown in FIGS. 3 and 4 of U.S. patent application Ser. No. 15/598,896. These views further depict the structures that may be employed to connect dosing syringe 8 with container 4. It is appreciated that either dosing syringe 8 or container 4 may be rotated with respect to each other to open a flow path between the two and dispense a quantity of fluid therebetween.

Shown in FIG. 3 is check valve mechanism 14 of dosing syringe 8. In particular, this end view shows key pin 32 and slots 24. Illustratively, key pin 32 may be generally cross-shaped. This shape produces a "key" function when engaged with receptacle 34 (see FIG. 4) of valve member 18 of closure valve 6. While key pin 32 is inserted into receptacle 34, tabs 25 on closure valve 6 are fitted into slots 24. Rotating either dosing syringe 8 or container 4 causes same to couple together while moving valve member 18 in direction 17 to engage surface 27 of valve member 46. This creates a passageway between the interior of dosing syringe 8 and the interior of container 4. Again, the mechanisms for moving valve member 18 are like those discussed in patent application Ser. No. 15/598,896 previously incorporated herein by reference. Surface 27 receives the force from valve member 18 to move valve member 46 also in direction 17 to create passage opening 50 (see, also, FIG. 2) which allows fluid to dispense fluid therefrom.

Figure 5:
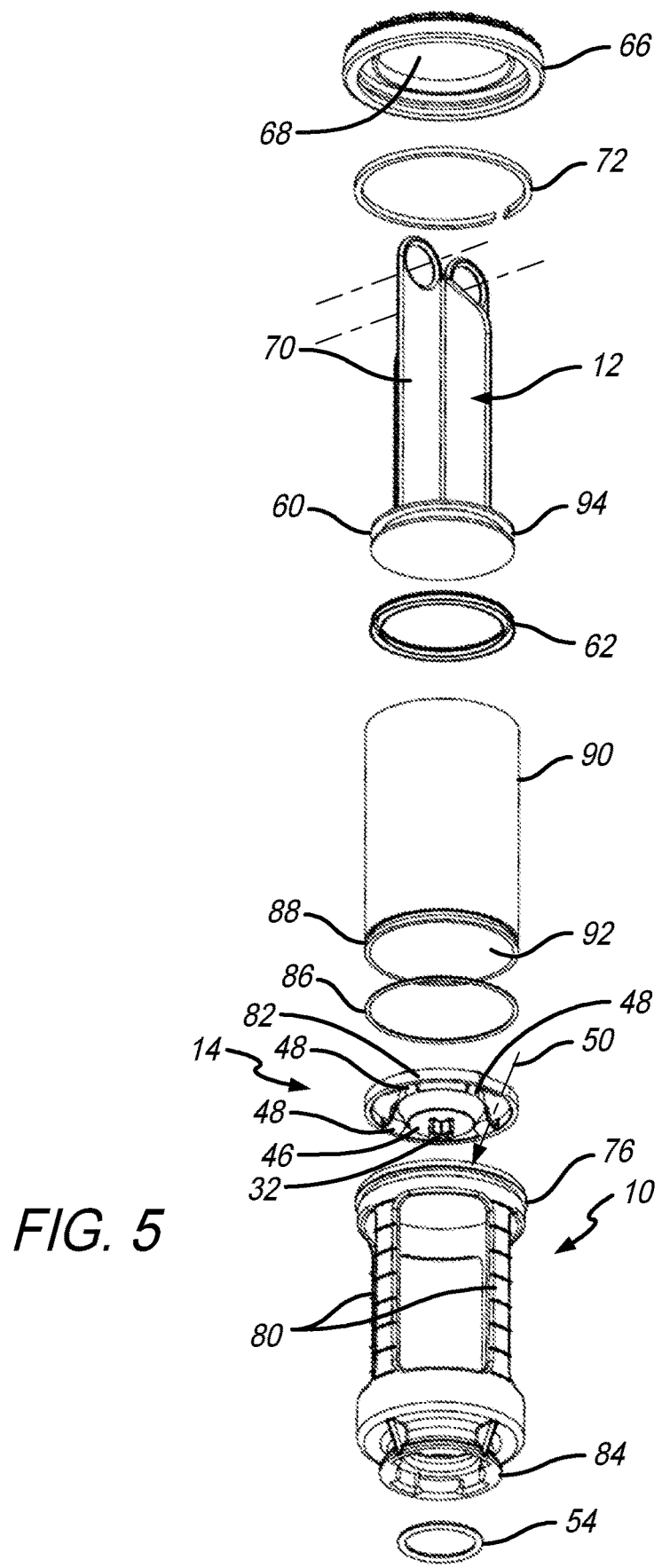
FIG. 5 is an exploded view of the adjustable dosing syringe.

An exploded view of adjustable dosing syringe 8 is shown in FIG. 5. As depicted, seal 54 is to be fitted onto syringe housing 10 (also shown in FIG. 2). Illustratively, check valve mechanism 14 fits into interior cavity 64. Illustratively, graduations 80 may extend along the side of syringe housing 10 to indicate volume segments of interior cavity 64. It is appreciated that syringe housing 10 and/or interior syringe cylinder 90 may each be clear and made from a plastic or glass material that allows an operator to observe the volume of fluid in interior cavity 64.

With respect to check valve mechanism 14, it includes spring legs 48, as shown, that allows valve member 46 to move with respect to syringe housing 10. Illustratively, valve member 46 may be cone-shaped so it moves to open passage opening 50 that extends from interior cavity 64 of syringe housing 10 to opening 40 (see FIGS. 2 and 3). This provides communication between syringe housing 10 and container 4. Check valve mechanism 14 also includes a valve base 82 that abuts base 84 of syringe housing 10 (see, also, FIG. 2) providing a seat for check valve mechanism 14. A seal 86 may set within gland 88 of interior syringe cylinder 90 and syringe housing 10 in the illustrative embodiments. Interior syringe cylinder 90 is located in interior cavity 64 and provides a fluid barrier in syringe housing 10. Interior syringe cylinder 90 also allows check valve mechanism 14 to be seated at base 84 of syringe housing 10. Illustratively, inner wall 92 of interior syringe cylinder 90 is the surface upon which seal 62 of plunger 12 engages to provide a fluid tight seal in interior syringe cylinder 90 between plunger 12 and the exterior of syringe assembly 8. It is appreciated that seal 62 may be a u-cup, O-ring, or other like sealing structure.

With further respect to plunger 12, seal 62 fits into cavity 94 of plunger base 60. Also shown is plunger stop 66 with opening 68 disposed therethrough to receive plunger arm 70. Retaining ring 72 engages both plunger stop 66 and syringe housing 10, including slot 76 (see, also, FIG. 2), to secure plunger stop 66 to syringe housing 10.

Figures 6, 7:
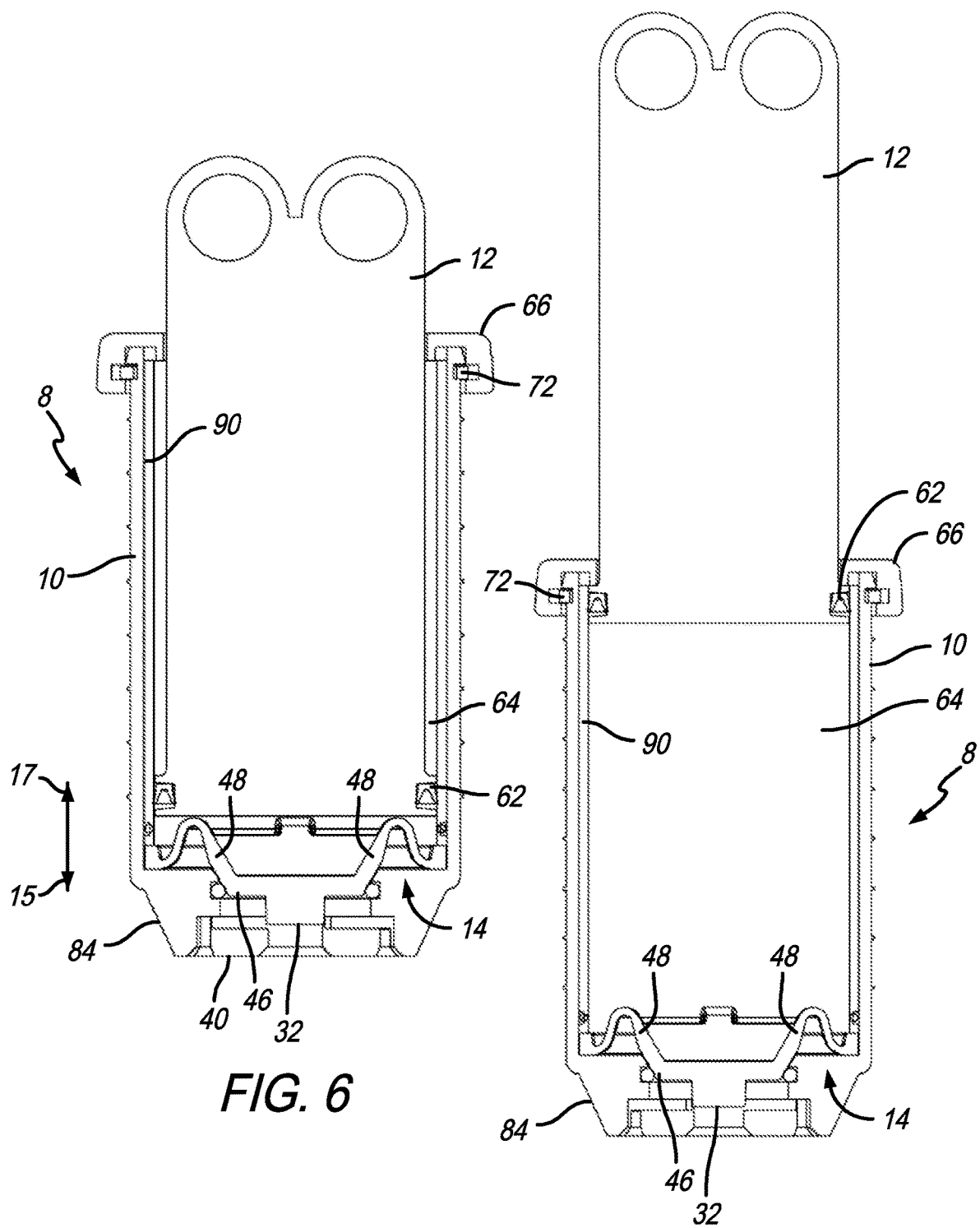
FIG. 6 is a cross-sectional elevational view of the dosing syringe.
FIG. 7 is another cross-sectional elevational view of the dosing syringe.

Cross-sectional elevation views of dosing syringe 8 are shown in FIGS. 6 and 7. The view shown in FIG. 6 depicts dosing syringe 8 with plunger 12 pushed fully in direction 15, thereby minimizing the volume of interior cavity 64. This is the position of plunger 12 when all of the fluid from interior cavity 64 is dispensed. As shown herein, valve member 46 is positioned in the closed position allowing no fluid communication through passage opening 50 and opening 40.

The cross-sectional view of FIG. 7 shows adjustable dosing syringe 8 with plunger 12 located in its open-most position with respect to interior cavity 64. Specifically, in this position, the maximum volume of interior cavity 64 is achieved. Again, it is appreciated that moving plunger 12 in direction 15 reduces the volume of interior cavity 64, whereas moving plunger 12 in direction 17 maximizes the volume.

Figure 8:
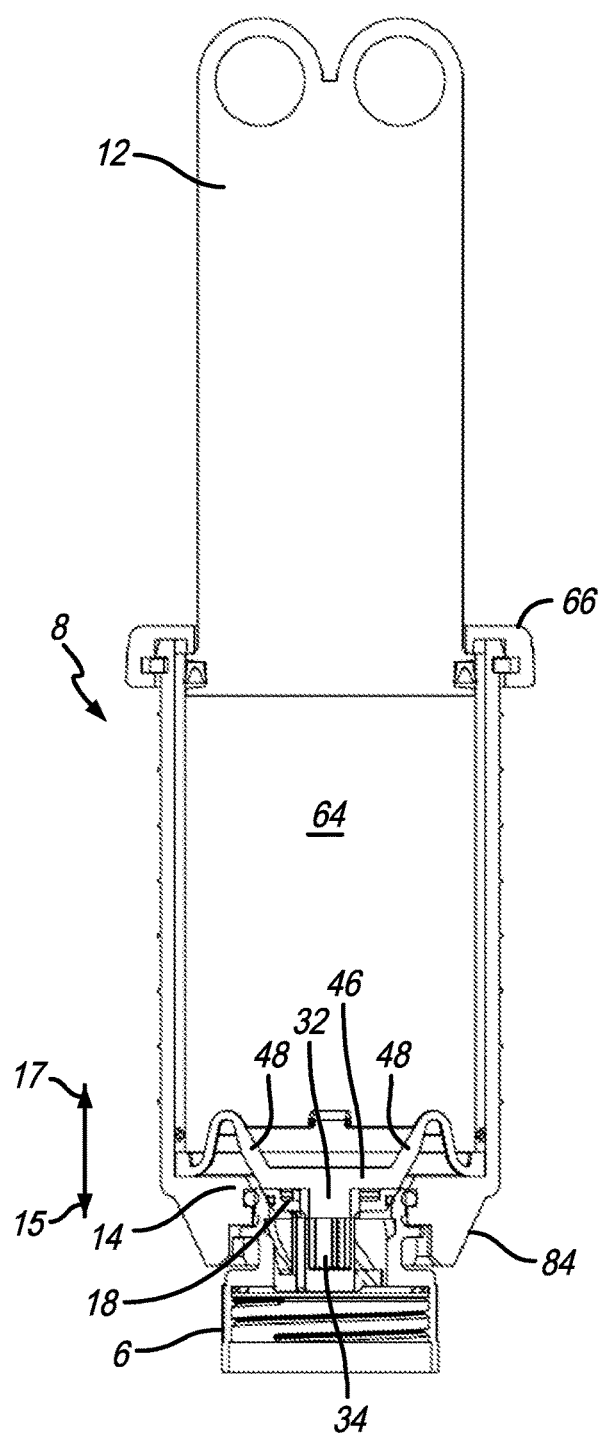
FIG. 8 is a cross-sectional elevational view of the dosing syringe connected to the closure valve.
Figure 9:
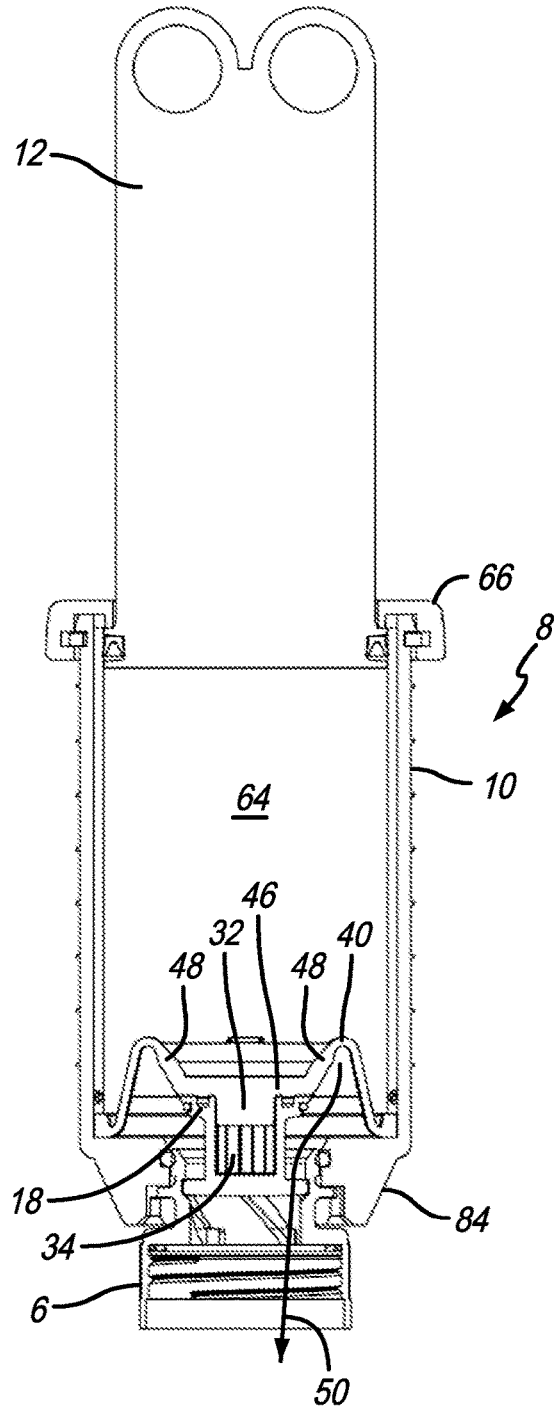
FIG. 9 is another cross-sectional elevational view of the dosing syringe connected to the closure valve.

Cross section elevational views of adjustable dosing syringe 8 are shown in FIGS. 8 and 9. FIG. 8 differs from FIG. 9 in that in FIG. 8, despite being connected to closure valve 6, valve member 46 is still located in its closed position. In FIG. 9 valve member 46 has been moved into its open position allowing fluid through passage opening 50 from interior cavity 64 and out of dosing syringe 8. This is accomplished by first extending key pin 32 of valve member 46 into receptacle 34 of valve member 18 of closure valve 6 as previously identified. The position of valve member 46 with respect to valve member 18, shown in FIG. 8, is a result of inserting key pin 32 of valve member 46 into receptacle 34 of valve member 18, but not yet rotating either dosing syringe 8 or container 4. As previously discussed with respect to check valve mechanism 14 and closure valve 6, in order to open valve member 46, either dosing syringe 8 or container 4 (with closure valve 6 attached) rotates. This extends valve member 18 in direction 17 (as explained in U.S. patent application Ser. No. 15/598,896) to push valve member 46 in direction 17, as well as forming passage opening 50 between interior cavity 64 and the interior of closure valve 6. At this point, plunger 12 may be pushed in direction 15 to reduce the volume of fluid in interior cavity 64 by pushing it through passage opening 50 into closure valve 6 and ultimately into container 4.

Figure 10:
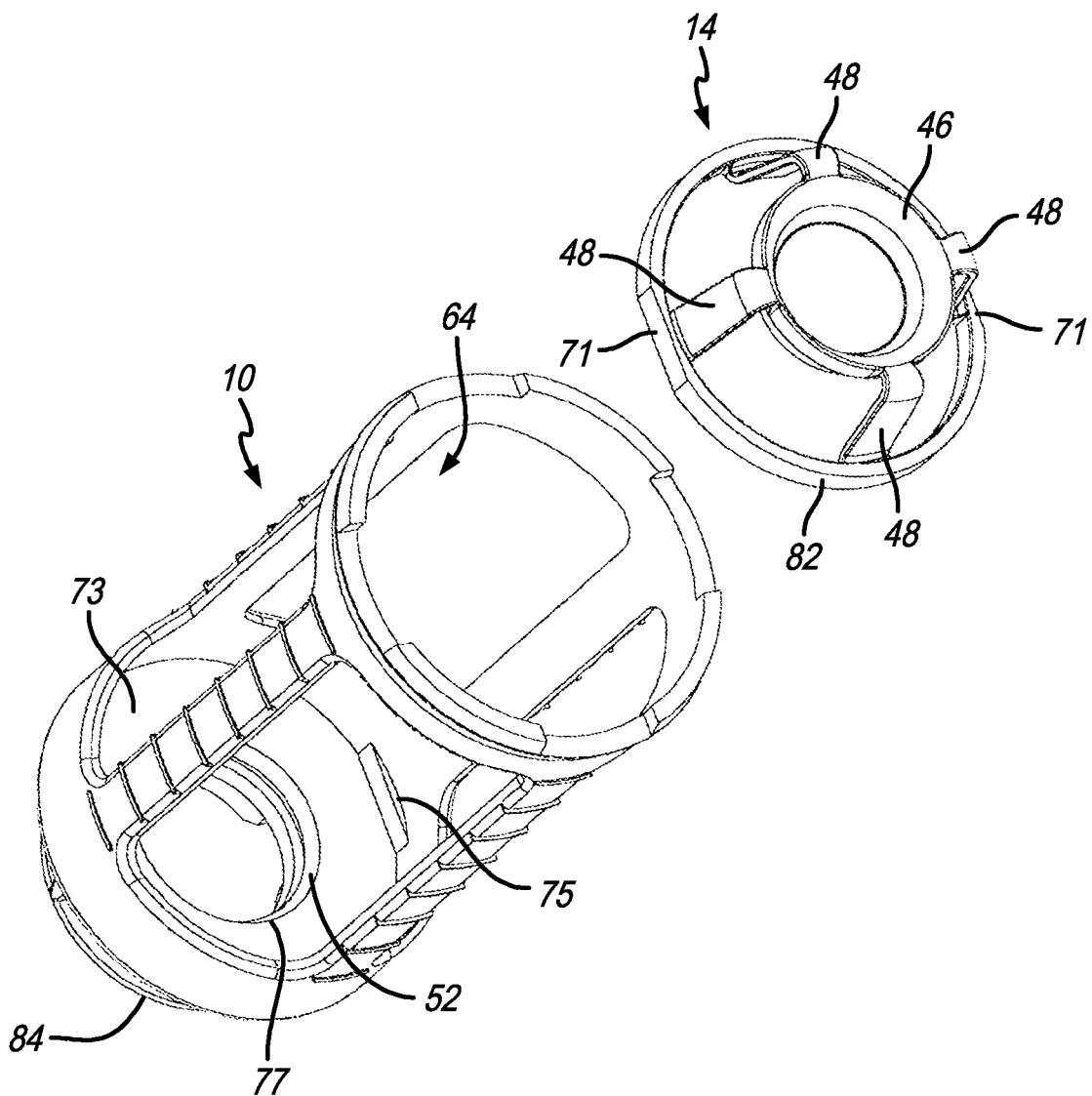
FIG. 10 is an exploded view of a syringe housing and check valve mechanism.

An exploded view of syringe housing 10 and check valve mechanism 14 is shown in FIG. 10. This view demonstrates how check valve mechanism 14 is fitted in interior cavity 64 of syringe housing 10. As shown, check valve mechanism 14 includes valve member 46 supported by spring legs 48 which are also connected to valve base 82. Key surfaces 71 are illustratively formed in valve base 82 as illustratively shown to assist in proper seating of syringe housing 10 onto valve base 82. Specifically, key surfaces 71 are illustratively flat surfaces, one on each side of check valve mechanism 14. Such flat surfaces interrupt the circular characteristics of valve base 82. Key surfaces 71 are configured to engage corresponding key members 75 (one of which is shown in FIG. 10) adjacent floor 73 of base 84. Such key surfaces 71 and key members 75 assist check valve mechanism 14 in seating properly onto valve base 82 of syringe housing 10. These structures also ensure that check valve mechanism 14 does not rotate with respect to syringe housing 10. With the assistance of the abutting keying structures, valve member 46 may be properly disposed in opening 77 formed by wall 52, as shown. This creates proper alignment so that key pin 32 of valve member 46 aligns with receptacle 34 of closure valve 6.

Figure 11:
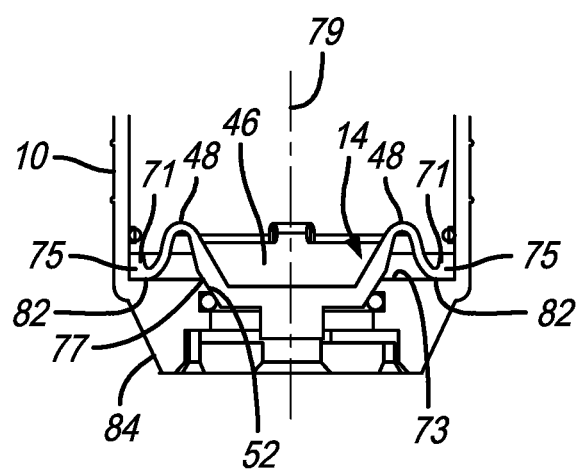
FIG. 11 is a detail cross-sectional view of a portion of the syringe housing and the check valve mechanism as disclosed herein.

A detail cross-sectional view of syringe housing 10, with check valve mechanism 14 disposed therein, is shown in FIG. 11. This view further depicts how key surfaces 71 illustratively oppose each other on valve base 82 and engage corresponding key members 75 also located opposite each other in syringe housing 10. Again, having these flat key surfaces 71 formed in an otherwise circular valve base 82, prevents check valve mechanism 14 from rotating about axis 79 when abutting corresponding key member 75 adjacent floor 73 of base 84 of syringe housing 10. This view further shows how valve member 46 fits into opening 77 in base 84 of syringe housing 10.

Figure 12:
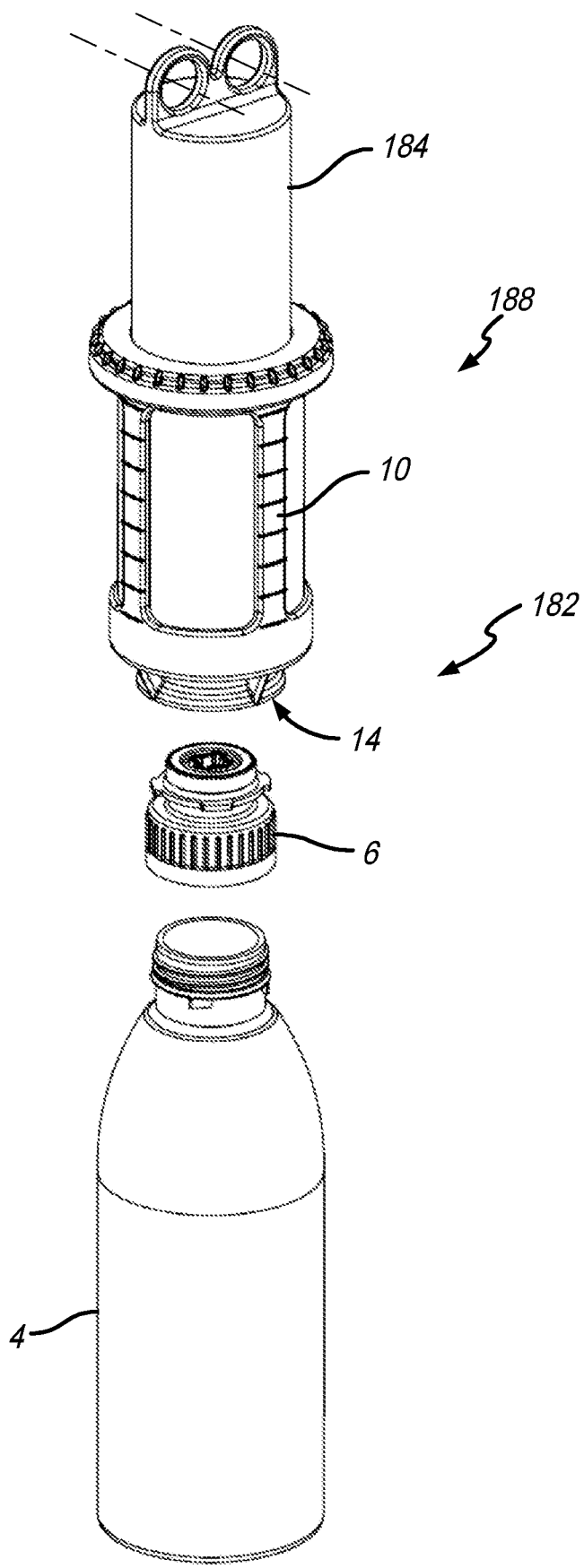
FIG. 12 is an exploded view of a telescoping metering syringe system according to another illustrative embodiment of the present disclosure.

Another illustrative embodiment of the present disclosure includes a telescoping metering system 182 as shown in FIG. 12. This embodiment is similar to the prior embodiment, except that an expanded plunger 184 is fitted into syringe housing 10 to form a telescoping dosing syringe 188. This provides an expanded volume capacity as compared to dosing syringe 8 shown in the prior embodiment. Otherwise, this embodiment also includes a container 4 with closure valve 6 attached thereto as first introduced in FIG. 2. Check valve mechanism 14 may also be coupled to syringe housing 10 of telescoping dosing syringe 188 similar to that described with respect to dosing syringe 8 of the prior embodiment.

Figure 13:
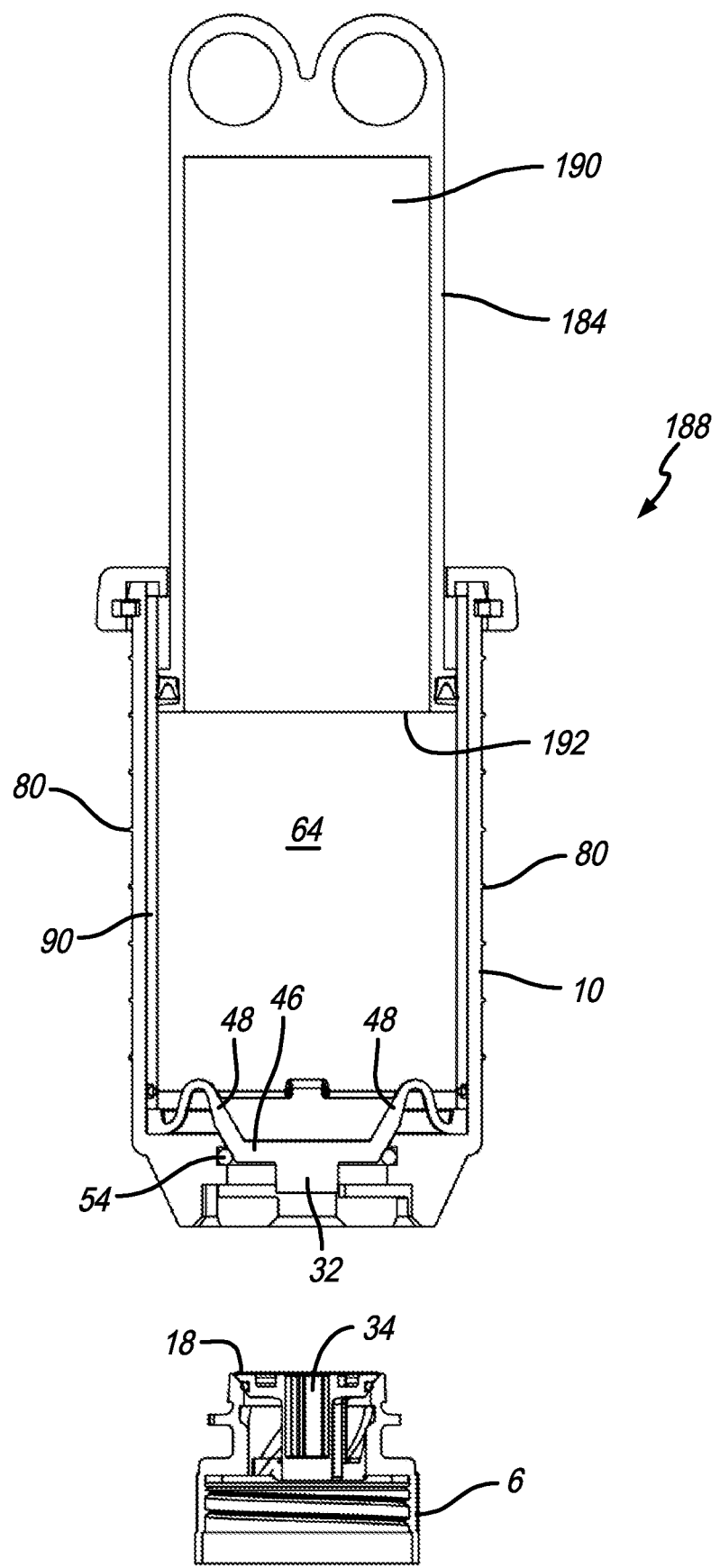
FIG. 13 is a cross-sectional view of the telescoping dosing syringe and the closure valve.

A cross-sectional view of telescoping dosing syringe 188, along with closure valve 6, is shown in FIG. 13. This view is similar to the view of FIG. 2. To that end, telescoping dosing syringe 188, like dosing syringe 8, includes check valve mechanism 14 that fits into interior cavity 64. Illustrative graduations 80 may extend along the side of syringe housing 10 to indicate volume segments of interior cavity 64. Like the prior embodiment, it is appreciated that syringe housing 10 and interior syringe cylinder 90 may be clear and made from a plastic or glass material to allow an operator to observe the fluid contents of interior cavity 64. It is also appreciated that check valve mechanism 14 includes spring legs 48 to allow valve member 46 to move with respect to syringe housing 10 like the prior embodiment. Again, valve member 46 may be cone-shaped to create passage opening 50 to extend from interior cavity 64 of syringe housing 10 to opening 40 (see, also, FIG. 2), thereby providing communication between syringe housing 10 and container 4. The other structures of check valve mechanism, previously described, may be included here as well.

It is further appreciated in FIG. 12 that expanded plunger 184 includes its own cavity 190 and opening 192 in fluid communication with interior cavity 64 of syringe housing 10. It will be appreciated by the skilled artisan upon reviewing this disclosure that a greater volume of fluid may be held by telescoping metering system 182 than by metering system 2. Specifically, fluid may fill both cavities 190 and 64 which provide the operator with an expanded range of usable fluid volume options available over dosing syringe 8 of the prior embodiment. In the circumstance with telescoping metering system 182, fluid can enter interior cavity 64 in the same manner as that described in the prior embodiment, but will first fill cavity 190 in expanded plunger 184. Then, additional fluid fills interior cavity 64. It will be appreciated that fluid inside cavities 190 and 64 may be dispensed in the same manner as that described in the prior embodiment. Fluid located in interior cavity 64 is dispensed first using the fluid in cavity 190 and gravity to push the fluid in interior cavity 64 through passage opening 50 and out of check valve mechanism 14. The fluid originally located in cavity 190 may then drain therefrom through an exit check valve mechanism 14 as well.

It should also be appreciated that check valve mechanism 14 and closure valve 6 of telescoping metering system 182 operate in the same manner as that described in the prior embodiment. Accordingly, check valve mechanism 14 and closure valve 6, as shown in FIGS. 3 and 4 of the prior embodiment, along with their descriptions, applied to check valve mechanism 14 and closure valve 6, are applied here in FIG. 13 of this embodiment.

Figure 14:
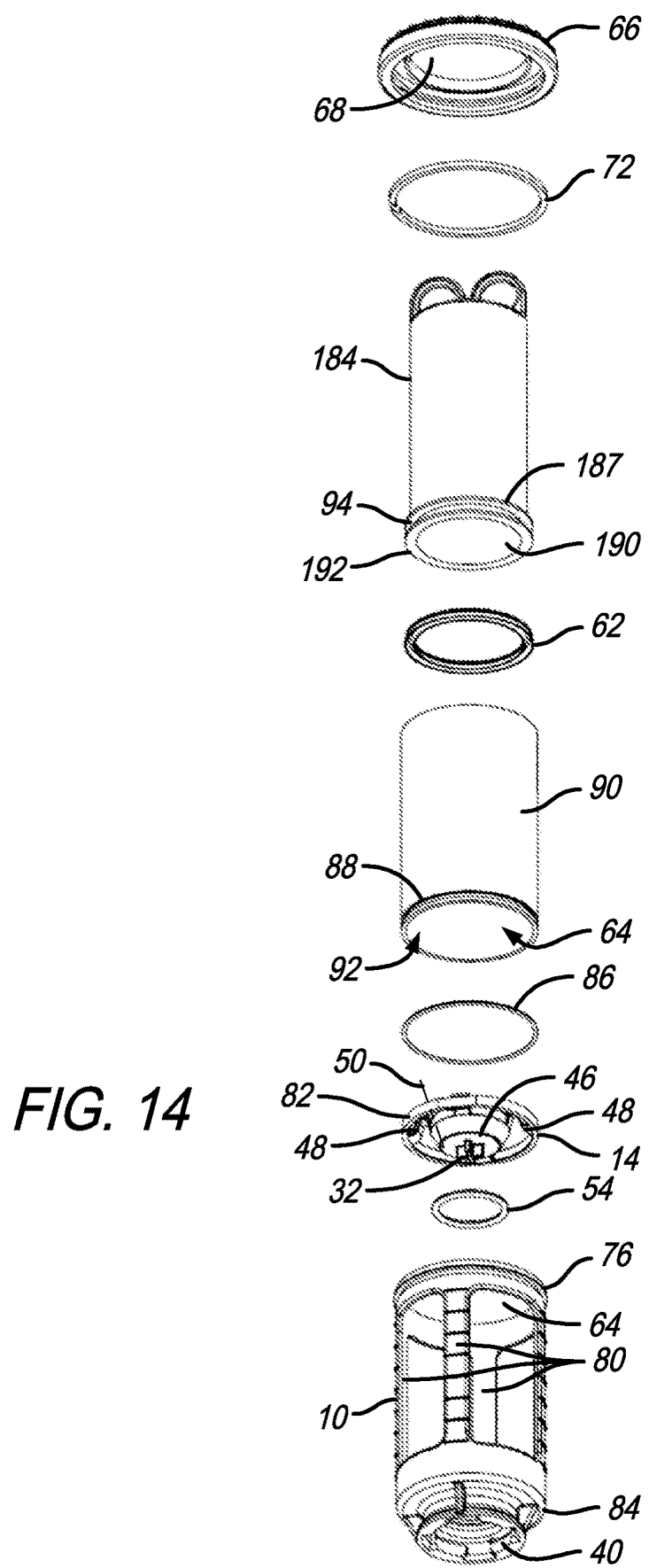
FIG. 14 is an exploded view of the telescoping dosing syringe.

An exploded view of telescoping dosing syringe 188 is shown in FIG. 14. This view is similar to that shown in FIG. 5 of the prior embodiment wherein seal 54 is to be fitted onto syringe housing 10 (as also shown in FIG. 13). Illustratively, check valve mechanism 14 fits into interior cavity 64. Graduations 80 may extend along the side of syringe housing 10 to indicate volume segments of interior cavity 64. Check valve mechanism 14 includes spring legs 48 that allow valve member 46 to move with respect to syringe housing 10. Valve member 46 may be cone-shaped which allows for passage opening 50 to extend from interior cavity 64 of syringe housing 10 to opening 40 (see, also, FIG. 13). This provides fluid communication between syringe housing 10 and container 4. Check valve mechanism 14 also includes valve base 82 that sits on base 84 of syringe housing 10 (see, also, FIG. 13) providing a seat for check valve mechanism 14. A seal 86 may be set in gland 88 of interior syringe cylinder 90 in the illustrative embodiment. Interior syringe cylinder 90 is located in interior cavity 64 and provides a fluid barrier in syringe housing 10. Interior syringe cylinder 90 also allows check valve mechanism 14 to be seated at base 84 of syringe housing 10. Inner wall 92 of interior syringe cylinder 90 is the surface upon which seal 62 of expanded plunger 184 engages to provide a fluid tight seal in syringe cylinder 90 between expanded plunger 184 and the exterior of telescoping dosing syringe assembly 188.

With respect to expanded plunger 184, seal 62 fits into cavity 94 of plunger base 187. Also shown is plunger stop 66 with opening 68 disposed therethrough to receive expanded plunger 184. Retaining ring 72 engages both plunger stop 66 and syringe housing 10, including slot 76, to secure plunger stop 66 to syringe housing 10. Expanded plunger 184 is shown with cavity 190 and opening 192. That said, seal 62 fits into cavity 94 at plunger base 194 of expanded plunger 184. Like the prior embodiment, retaining ring 72 engages both plunger stop 66 and syringe housing 10 to secure plunger stop 66 to syringe housing 10.

Elevational cross-sectional views of telescoping dosing syringe 188 are shown in FIGS. 15 and 16, respectively. These views demonstrate how the volume of fluid may change when expanded plunger 184 has moved downward in syringe housing 10 in direction 15. As shown in FIG. 15, similar to the view in FIG. 13, both cavities 190 and 64 are available to receive fluid. Again, this expands the relative amount of fluid that can be received in telescoping dosing syringe 188 as compared to dosing syringe 8 of the prior embodiment. FIG. 16 depicts expanded plunger 184 disposed into interior cavity 64. As previously identified, any fluid in interior cavity 64 will be pushed out of check valve mechanism 14 via fluid in cavity 190 of expanded plunger 184. The remaining fluid originally in expanded plunger 184 is then also able to drain through check valve mechanism 14.

Figure 17:
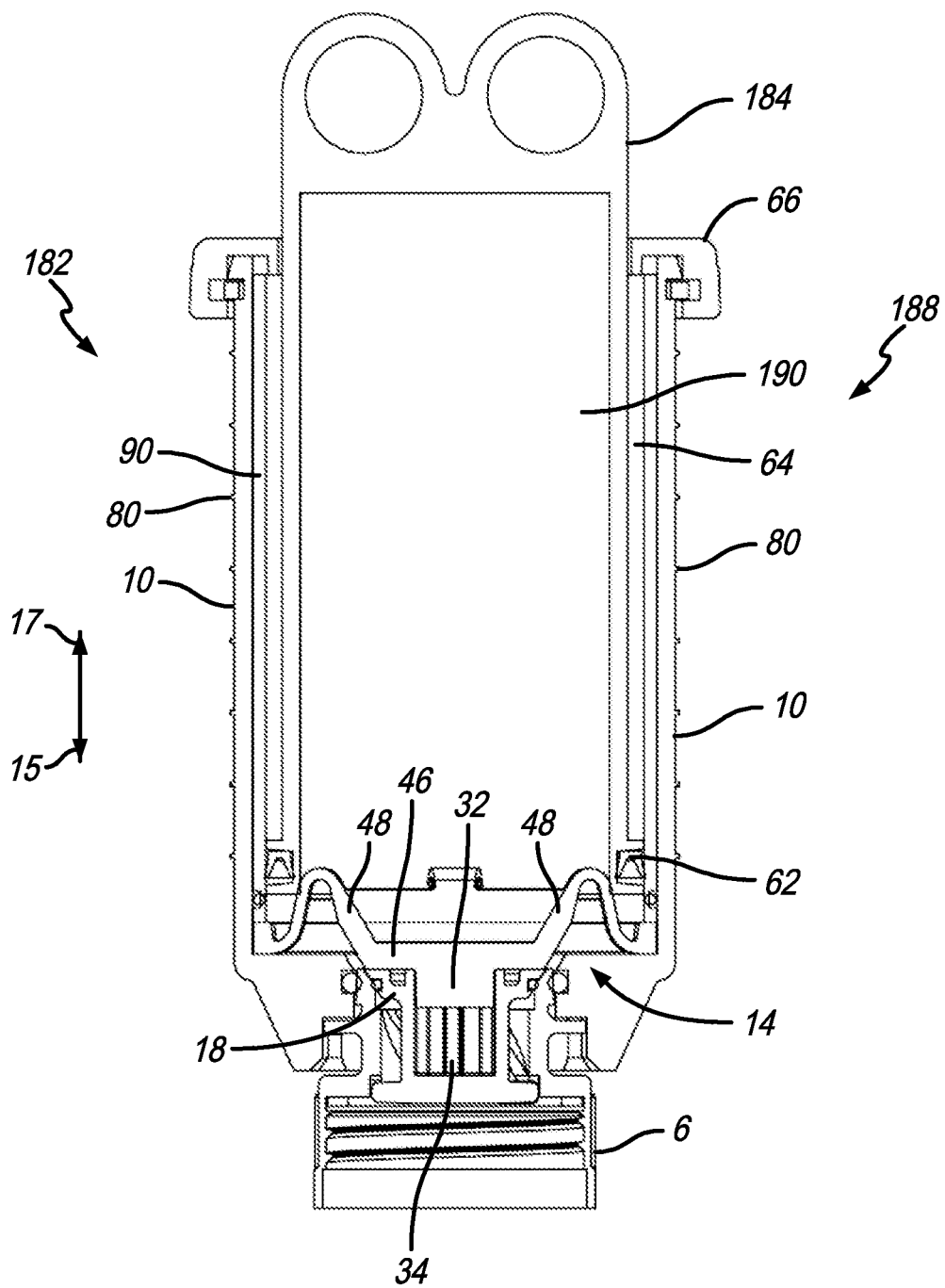
FIG. 17 is an elevational cross-sectional view of the telescoping dosing syringe coupled to the closure valve.
Figure 18:
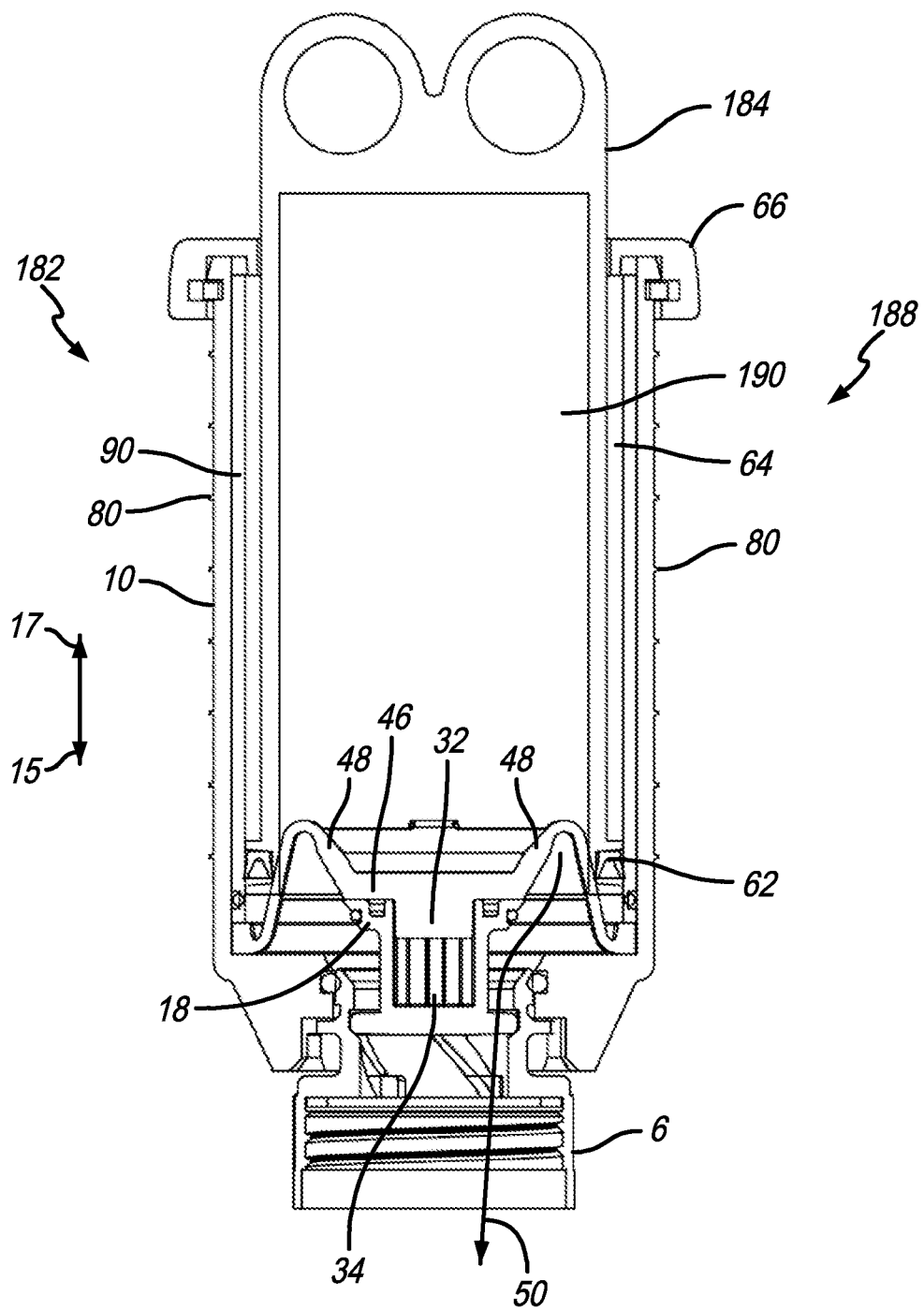
FIG. 18 is another elevational cross-sectional view of the telescoping dosing syringe coupled to the closure valve.

Elevational cross-sectional views of telescoping dosing syringe 188, coupled to closure valve 6, are shown in FIGS. 17 and 18. The view in FIG. 17 depicts check valve mechanism 14 coupled to closure valve 6 in the manner previously discussed with regard to FIGS. 8 and 9. In FIG. 17, valve member 46 is still in its closed position, but with key pin 32 disposed in receptacle 34 of valve member 18 of closure valve 6. In this instance, no fluid can yet transfer from either cavity 190 or 64. But, if either telescoping dosing syringe 188 or closure valve 6 is rotated with respect to the other structure, as previously described, valve member 18 is moved in direction 17 to create passage opening 50. Such is illustrated by FIG. 18. By creating passage opening 50, fluid is allowed to flow between the interior of telescoping dosing syringe 188 and closure valve 6.

Another illustrative embodiment of the present disclosure again dispenses fluid similar to the prior embodiment. A syringe operatively connects to a container so that valves between the syringe and container operatively cooperate to selectively open and create a fluid path between the syringe and the container. The fluid is then dispensed into the container through the fluid path from the syringe. In this illustrative embodiment, however, a selective dose dispensing assembly is provided to the syringe.

Figure 19:
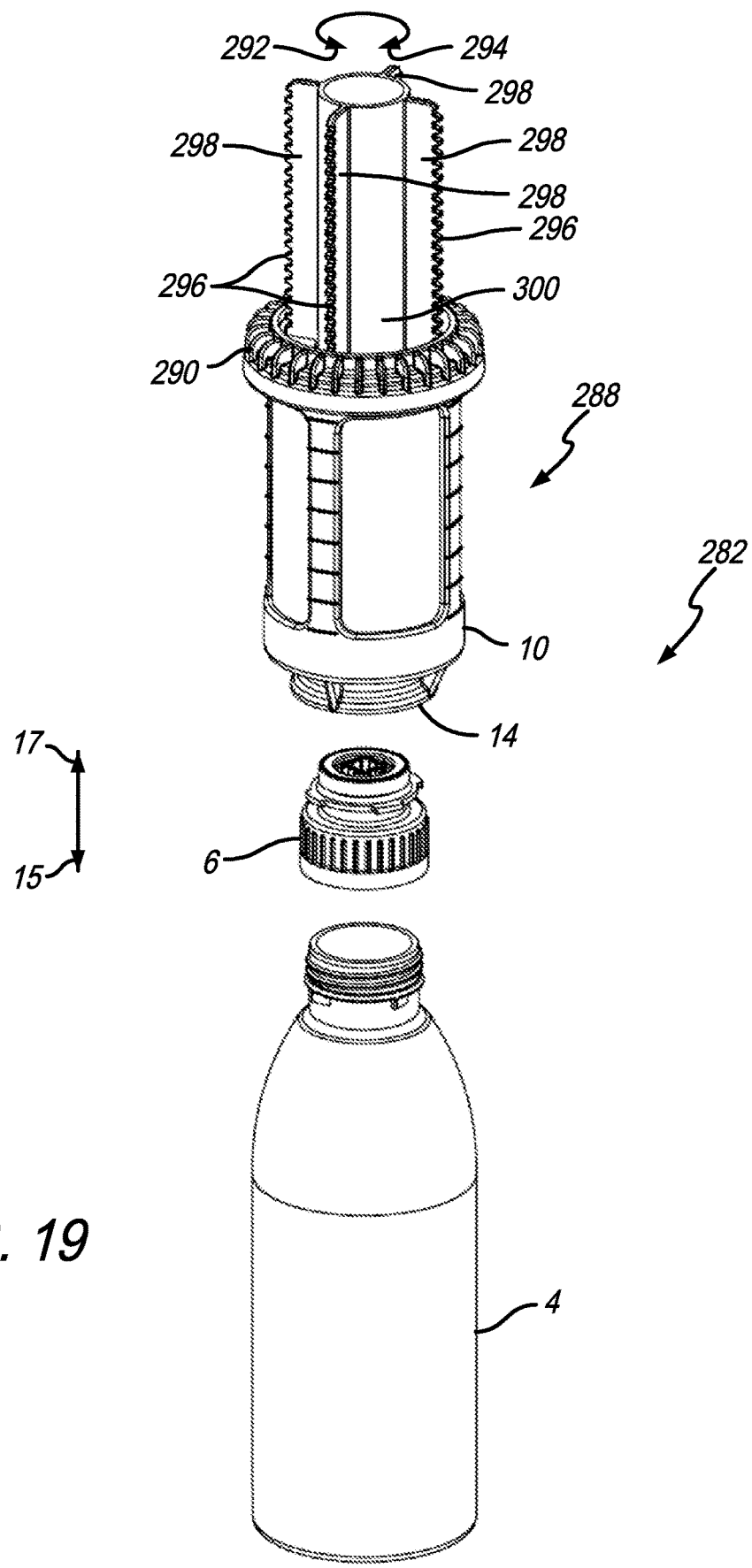
FIG. 19 is an exploded view of the illustrative selective dose dispensing assembly.

Accordingly, an exploded view of an illustrative selective dose dispensing assembly 282 is shown in FIG. 19. This creates precision as to how much fluid the syringe may receive. Here, like the prior embodiments, a container 4 is configured to receive closure valve 6. In contrast, however, selective dose dispensing assembly 282 includes selective dosing syringe 288 which is configured to selectively limit the volume capacity in selective dosing syringe 288. To that end, only a specific (i.e., precise) amount of fluid can enter selective dosing syringe 288 to be dispensed into or received from container 4. In this illustrative embodiment, an adjustment collar 290 is configured to be rotatable in either directions 292 or 294. Teeth or serrations 296 are located on flanges 298 of plunger 300. Teeth 296 are configured to engage adjustment collar 290 so that rotation of same moves plunger 300 in either direction 15 or 17 within syringe housing 10 to limit the volume capacity within same.

Figure 20:
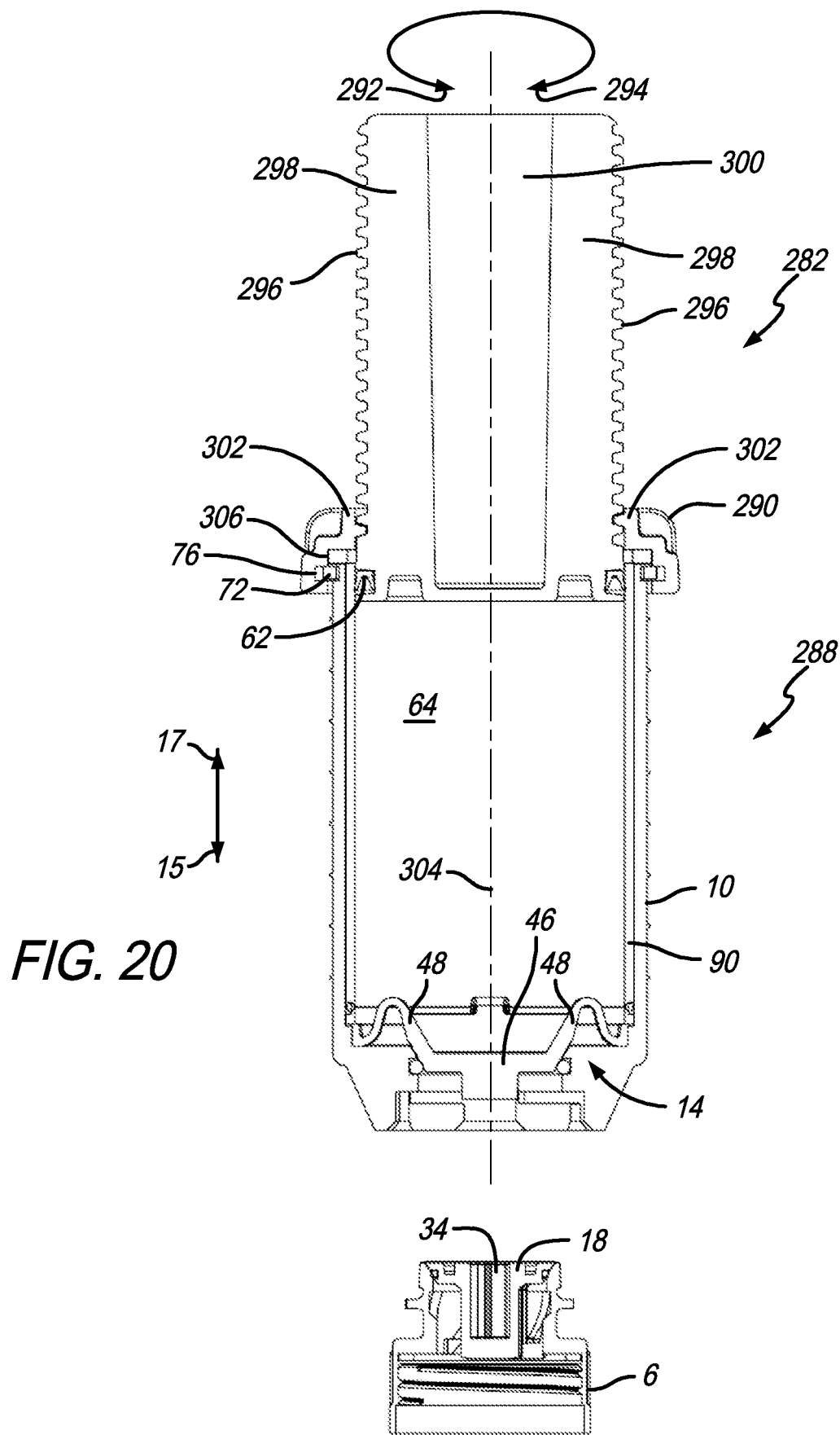
FIG. 20 is an elevational cross-sectional view of the selective dosing syringe, plunger, and closure valve.

An elevational cross-sectional view of selective dosing syringe 288, plunger 300, and closure valve 6, is shown in FIG. 20. This view further depicts teeth or serrations 296 located on flanges 298 of plunger 300 being engagable with corresponding threads 302 of adjustment collar 290. Rotating adjustment collar 290 about axis 304 in either direction 292 or 294 will move plunger 300 in either direction 15 or 17 within interior cavity 64 of syringe housing 10. It is appreciated that threads 302 may be angled so that such rotation of adjustment collar 290 about axis 304 in directions 292 or 294 will raise or lower plunger 300 in direction 17 or 15, respectively, as desired. Also shown is a key 306 configured to keep flanges 298 of plunger 300 from rotating as they enter and exit interior cavity 64 of syringe cylinder 90 and syringe housing 10.

Figure 21:
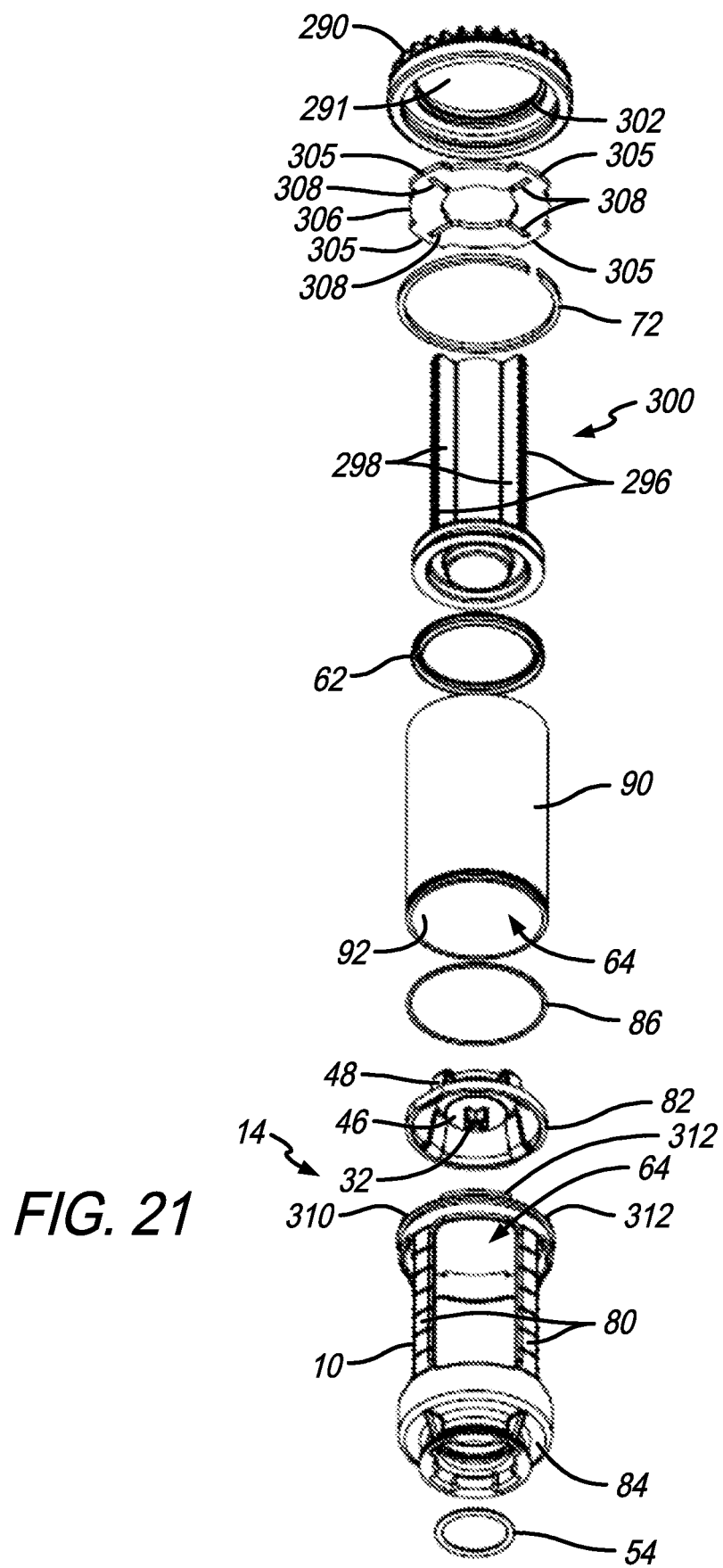
FIG. 21 is an exploded view of the selective dosing syringe.

An exploded view of selective dosing syringe 288 is shown in FIG. 21. Seal 54 is to be fitted onto syringe housing 10 like the prior embodiments. Illustratively, check valve mechanism 14 also fits into interior cavity 64. Again, graduations 80 may extend along the side of syringe housing 10 to indicate volume segments within interior cavity 64.

Check valve mechanism 14, also part of selective dosing syringe 288, includes spring legs 48 that allow valve member 46 to move with respect to syringe housing 10. Illustratively, valve member 46 may be cone-shaped so it moves to open a passageway such as passage opening 50 as shown in FIG. 18 from the prior embodiment. And as previously discussed, this provides communication between syringe housing 10 and container 4. Check valve mechanism 14 also includes a valve base 82 that abuts base 84 of syringe housing 10. This provides a sealing seat for check valve mechanism 14. Like the prior embodiments, a seal 86 may set within gland 88 of syringe cylinder 90 and syringe housing 10 in this illustrative embodiment. Interior syringe cylinder 90 is located in interior cavity 64 and provides a fluid barrier in syringe housing 10. Interior syringe cylinder 90 also allows check valve mechanism 14 to be seated at base 84 of syringe housing 10. Inner wall 92 of interior syringe cylinder 90 is the surface upon which seal 62 of plunger 300 engages. This provides a fluid tight seal between syringe cylinder 90 and plunger 300.

Also shown with respect to plunger 300 is adjustment collar 290 with opening 291 through which flanges 298 of plunger 300 are configured to extend through. Also, threads 302 are shown at the periphery of opening 291 and configured to engage teeth or serrations 296 on flanges 298. As discussed, adjustment collar 290, with its threads 302, is configured such that rotating same will move plunger 300 linearly. Key 306 illustratively includes slots 308 sized to receive corresponding flanges 298 of plunger 300. Tabs 305 extend from the perimeter of key 306. About top periphery 310 of syringe housing 10 includes periodically spaced upward extending tabs 312. These tabs 312 fit between tabs 305 of key 306. This allows key 306 to sit onto top periphery 310 and be prevented from rotating relative thereto (see, also, FIG. 22). Lastly, retaining ring 72, similar to the retaining rings of the prior embodiments, engages both adjustment collar 290 and syringe housing 10, coupling both together. It is appreciated, however, that by making such connection illustratively as shown, forming a slot 76 (see, also, FIG. 20), adjustment collar 290 is not inhibited from rotating in directions 292 or 294 despite connecting with syringe housing 10.

Figure 22:
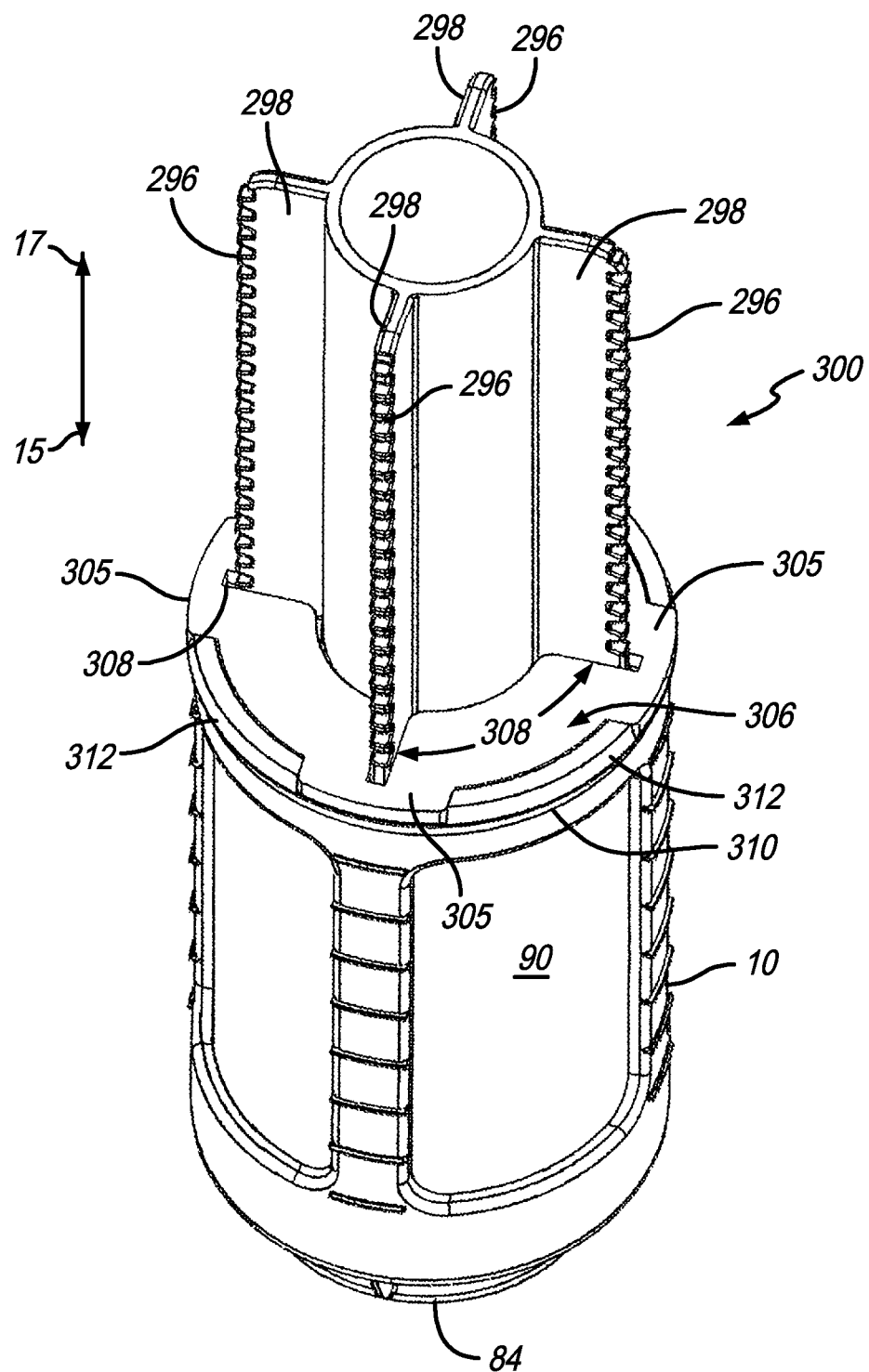
FIG. 22 is a prospective view of the plunger disposed in the syringe cylinder and syringe housing.

A perspective view of plunger 300, disposed in syringe cylinder 90 and syringe housing 10, is shown in FIG. 22. Particularly, this view depicts how key 306 is fitted onto syringe housing 10 so as not to rotate plunger 300 while it is moving into and out of syringe cylinder 90. Here, tabs 305 of key 306 are fitted between upward extending tabs 312 from top periphery 310 of syringe housing 10. This engagement prevents key 306 from pivoting or rotating with respect to syringe housing 10 while plunger 300 is movable into and out of syringe housing 10 in directions 15 and 17. By preventing plunger 300 from rotating adjustment collar 290 (see, also, FIG. 23), the engagement as further discussed herein between plunger 300 and rotating adjustment collar 290 will allow plunger 300 to only move linearly, not rotationally.

Figure 23:
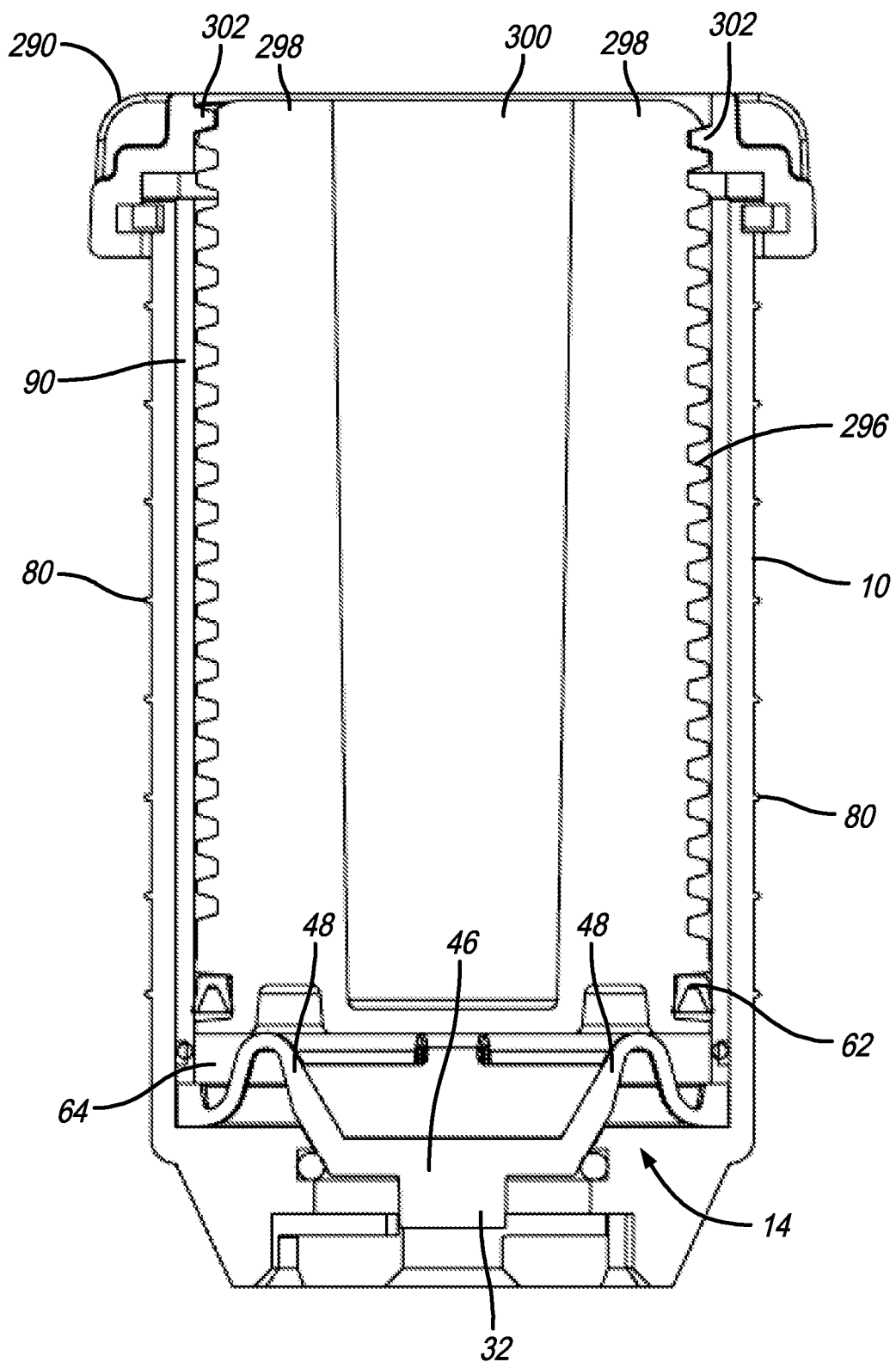
FIG. 23 is an elevational cross-sectional view of the selective dosing syringe.

An elevational cross-sectional view of selective dosing syringe 288 is shown in FIG. 23. Here, plunger 300 is shown disposed in syringe housing 10 to reduce the available fluid volume in interior cavity 64 and to dispense same out of opening 40 of check valve mechanism 14. Plunger 300 is moved to this position by rotating adjustment collar 290, as previously discussed. This translation from rotational movement to linear movement allows precise volumetric adjustments of selective dosing syringe 288. For example, rotating adjustment collar 290 in small increments allows making precise volumetric changes in interior cavity 64. This means, under circumstances where a precise amount of fluid is needed to be transferred, that precise volume can be metered in interior cavity 64 within syringe housing 10 by rotating adjustment collar 290—thereby moving plunger 300.

Figure 24:
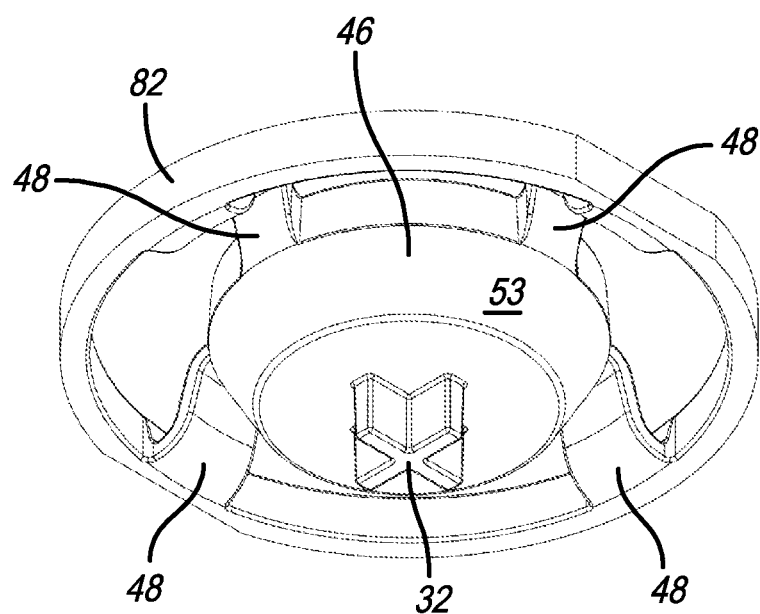
FIG. 24 is a prospective view of a valve member portion of the selective dosing syringe.

A perspective view of valve member 46, that is part of check valve mechanism 14, is shown in FIG. 24. Sitting at the periphery of valve member 46 are spring legs 48 as previously discussed. As shown, springs legs 48 connect valve member 46 with valve base 82. Key pin 32 extends from valve member 46 as shown. In the illustrative embodiment, valve member 46 has a chamfered surface 53 which engages seal 54 as shown in the prior embodiments, in order to produce a seal between valve member 46 and base 84 of syringe housing 10. This prevents fluid from escaping any of the embodiments of the syringes unless valve member 46 is moved by valve member 18 of closure valve 6 to the open position.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the present disclosure.

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features. It should also be appreciated that if any subject matter disclosed in this non-provisional Patent Application differs from the priority Application the disclosure from this non-provisional Patent Application controls.

What is claimed is:

1. A metered dosing assembly configured to dispense a volume of fluid into a container that is selectively sealed by a closure valve having a closure valve member that is movable between sealed and unsealed positions with respect to the container, the metered dosing assembly comprises:
    a housing having an interior cavity and first and second ends;
    a plunger base selectively locatable adjacent the first end of the housing;
    wherein the plunger base is movable within the interior cavity of the housing to change the size of the interior cavity that holds the volume of fluid; a plunger arm that extends from the plunger base and an exterior of the first end of the housing to move the plunger base within the interior cavity to change the size of the interior cavity that holds the volume of fluid; a stop located adjacent the first end of the housing to limit movement of the plunger base inside the interior cavity of the housing; and
    a valve locatable at the second end of the housing;
    wherein the valve includes a valve member, a pin extending from the valve member, and at least one spring leg attachable to the valve member;
    wherein the pin extending from the valve member is configured to engage the closure valve member to move the closure valve member to the unsealed position;
    wherein the at least one spring leg is movable further into the interior cavity of the housing such that the valve member is movable to an open position with respect to the housing when the pin extending from the valve member is engaged with the closure valve member of the closure valve; and
    wherein when the valve member is moved to the open position and the closure valve member is moved to the unsealed position, fluid communication is made between the metered dosing assembly and the container.

2. The metered dosing assembly of claim 1, further comprising a seal member located between the plunger base and an interior wall of the interior cavity of the housing.

3. The metered dosing assembly of claim 1, wherein the at least one spring leg is a plurality of spring legs.

4. The metered dosing assembly of claim 1, further comprising a base located at the second end of the housing, wherein the base includes an opening to exterior of the housing, and wherein the valve member of the valve is movable with respect to the opening between the open position and a closed position.

5. The metered dosing assembly of claim 1, wherein the valve further includes a valve base that encircles at least a portion of the valve member, the at least one spring leg, and a space locatable adjacent the valve member and the at least one spring leg.

6. The metered dosing assembly of claim 1, wherein the housing includes a key structure and the valve includes a key structure corresponding to the key structure of the housing, wherein the key structure of the housing abuts the key structure of the valve to limit the positioning of the valve within the interior cavity of the housing.

7. The metered dosing assembly of claim 1, wherein the plunger arm includes a second interior cavity that is in fluid communication with the interior cavity of the housing to increase a total volume size of the metered dosing assembly available to hold the volume of fluid.

8. The metered dosing assembly of claim 1, wherein the plunger arm includes a plurality of teeth configured to engage at least one thread on a collar movably secured to the housing such that as the at least one thread on the collar moves, the plunger arm and plunger base move to change the size of the interior cavity that holds the volume of fluid.

9. The metered dosing assembly of claim 8, further comprising a key member located adjacent the first end of the housing, wherein the key member includes an opening that receives at least a portion of the plunger arm and at least one tab that engages at least one portion of the housing, wherein as the at least one thread on the collar moves, the collar rotates to move the plunger base linearly within the interior cavity of the housing, and wherein the key member located adjacent the first end of the housing prevents the plunger arm and plunger base from rotating with the collar.

10. The metered dosing assembly of claim 1, wherein the plunger arm includes a plurality of flanges and each of the plurality of flanges includes a plurality of teeth, each of the plurality of teeth on the plurality of flanges is configured to engage at least one thread on a collar such that as the at least one thread on the collar moves, the plunger arm and plunger base move to change the size of the interior cavity that holds the volume of fluid.

11. A metered dosing assembly configured to dispense a volume of fluid into a container that is selectively sealed by a closure valve having a closure valve member that is movable between sealed and unsealed positions with respect to the container, the metered dosing assembly comprises:

a housing having an interior cavity and first and second ends;

a plunger base selectively locatable adjacent the first end of the housing;

wherein the plunger base is movable within the interior cavity of the housing to change the size of the interior cavity that holds the volume of fluid; a plunger arm that extends from the plunger base and an exterior of the first end of the housing to move the plunger base within the interior cavity to change the size of the interior cavity that holds the volume of fluid; a stop located adjacent the first end of the housing to limit movement of the plunger base inside the interior cavity of the housing; and a valve with at least one spring leg, wherein the valve is locatable at the second end of the housing;

wherein the valve includes a valve member; and wherein the at least one spring leg is movable further into the interior cavity of the housing such that when the valve member is moved to an open position and the closure valve member is moved to the unsealed position, fluid communication is made between the metered dosing assembly and the container.

12. The metered dosing assembly of claim 11, wherein a plunger arm extends from the plunger base and exterior of the first end of the housing to move the plunger base within the interior cavity to change the size of the interior cavity that holds the volume of fluid.

\* \* \* \* \*